(12) United States Patent
Tomar et al.

(10) Patent No.: US 11,465,999 B2
(45) Date of Patent: Oct. 11, 2022

(54) PROCESS FOR PREPARING ALECTINIB OR A PHARMACEUTICALLY ACCEPTABLE SALT THEREOF

(71) Applicant: FRESENIUS KABI ONCOLOGY LIMITED, New Delhi (IN)

(72) Inventors: Vinod Singh Tomar, Gurgaon Haryana (IN); Abul Azim, Gurgaon Haryana (IN); Nitin Gupta, Gurgaon Haryana (IN); Saswata Lahiri, Gurgaon Haryana (IN); Walter Cabri, Cernusco sul Naviglio—Milano (IT)

(73) Assignee: FRESENIUS KABI ONCOLOGY LTD., New Delhi (IN)

( * ) Notice: Subject to any disclaimer, the term of this patent is extended or adjusted under 35 U.S.C. 154(b) by 0 days.

(21) Appl. No.: 17/403,751

(22) Filed: Aug. 16, 2021

(65) Prior Publication Data
US 2021/0371410 A1    Dec. 2, 2021

Related U.S. Application Data

(62) Division of application No. 16/627,160, filed as application No. PCT/IB2018/054932 on Jul. 4, 2018, now Pat. No. 11,098,037.

(30) Foreign Application Priority Data

Jul. 5, 2017  (IN) .......................... IN201711023632

(51) Int. Cl.
C07D 413/14    (2006.01)
B01J 31/04     (2006.01)
B01J 31/12     (2006.01)
B01J 31/24     (2006.01)

(52) U.S. Cl.
CPC ............ C07D 413/14 (2013.01); B01J 31/04 (2013.01); B01J 31/122 (2013.01); B01J 31/2404 (2013.01); B01J 2231/44 (2013.01); B01J 2531/824 (2013.01); C07B 2200/13 (2013.01)

(58) Field of Classification Search
CPC .............................. C07D 413/14; B01J 31/04
See application file for complete search history.

(56) References Cited

U.S. PATENT DOCUMENTS

| | | |
|---|---|---|
| 9,126,931 B2 | 9/2015 | Kinoshita et al. |
| 9,365,514 B2 | 6/2016 | Furumoto et al. |
| 9,440,922 B2 | 9/2016 | Kinoshita et al. |
| 9,573,932 B2 | 2/2017 | Xu |
| 10,221,155 B2 | 5/2019 | Xu |
| 10,344,014 B2 | 7/2019 | Shiraki et al. |
| 10,646,468 B2 | 5/2020 | Furumoto et al. |
| 11,014,919 B2 | 5/2021 | Cabri et al. |
| 2012/0083488 A1 | 4/2012 | Kinoshita et al. |
| 2013/0143877 A1 | 6/2013 | Furumoto et al. |
| 2015/0150845 A1 | 6/2015 | Kinoshita et al. |
| 2016/0257667 A1 | 9/2016 | Xu |
| 2016/0317494 A1 | 11/2016 | Furumoto et al. |
| 2016/0340308 A1 | 11/2016 | Kinoshita et al. |
| 2017/0217927 A1 | 8/2017 | Shiraki et al. |
| 2019/0284163 A1 | 9/2019 | Shiraki et al. |
| 2020/0017442 A1 | 1/2020 | Kinoshita et al. |
| 2020/0140427 A1 | 5/2020 | Tomar et al. |
| 2020/0181133 A1 | 6/2020 | Cabri et al. |

FOREIGN PATENT DOCUMENTS

| | | |
|---|---|---|
| CN | 105777710 A | 7/2016 |
| CN | 106518842 A | 3/2017 |
| CN | 106892861 A | 6/2017 |
| CN | 106905226 A | 6/2017 |
| CN | 106928125 A | 7/2017 |
| CN | 106928185 A | 7/2017 |
| CN | 106995433 A | 8/2017 |
| CN | 107011245 A | 8/2017 |
| CN | 107129488 A | 9/2017 |
| CN | 107987056 A | 5/2018 |
| CN | 108033947 A | 5/2018 |
| CN | 108178743 A | 6/2018 |
| CN | 108314674 A | 7/2018 |
| CN | 108264476 A | 10/2018 |
| CN | 109293629 A | 2/2019 |
| CN | 109384664 A | 2/2019 |
| CN | 109438218 A | 3/2019 |
| CN | 106892860 B | 8/2019 |
| CN | 106928184 B | 9/2019 |
| CN | 107033124 B | 9/2019 |
| CN | 107033125 B | 9/2019 |
| EP | 2 441 753 A1 | 4/2012 |
| EP | 3 135 671 A1 | 3/2017 |
| EP | 3 556 754 A1 | 10/2019 |

(Continued)

OTHER PUBLICATIONS

Anonymous, "Preparation of 9-ethyl-6,6-dimethyl-8-(4-morpholinopiperidin-1-yl)-11-oxo-6,11-dihydro-5H-benzo[b]carbazole-3-carbonitrile", IP.com Journal 17(7A): 1-2 (2017).

Austin et al., "Facile synthesis of ethynylated benzoic acid derivatives and aromatic compounds via ethynyltrimethylsilane," J. Org. Chem., 46(11): 2280-2286 (1981).

Flick et al., "Synthetic approaches to the 2014 new drugs," Bioorg. Med. Chem., 24(9): 1937-1980 (2016).

Herbert, "Negishi-type coupling of bromoarenes with dimethylzinc," Tet. Let., 45:817-819 (2004).

(Continued)

Primary Examiner — Kamal A Saeed
(74) Attorney, Agent, or Firm — Leydig, Voit & Mayer, Ltd.

(57) ABSTRACT

The present invention relates to a process for preparing the Alectinib or a pharmaceutically acceptable salt thereof using lesser reaction steps and also eliminating expensive and time-consuming column chromatography. The invention also relates to novel polymorphic forms of Alectinib and Alectinib hydrochloride.

23 Claims, 7 Drawing Sheets

(56) References Cited

FOREIGN PATENT DOCUMENTS

| IN | 201741044856 A | 6/2019 |
|---|---|---|
| WO | WO 2010/143664 A1 | 12/2010 |
| WO | WO 2012/023597 A1 | 2/2012 |
| WO | WO 2015/163447 A1 | 10/2015 |
| WO | WO 2016/021707 A1 | 2/2016 |
| WO | WO 2019/008520 A1 | 1/2019 |
| WO | WO 2019/038779 A1 | 2/2019 |
| WO | WO 2019/211868 A1 | 11/2019 |

OTHER PUBLICATIONS

Hughes, "Patent Review of Manufacturing Routes to Recently Approved Oncology Drugs: Ibrutinib, Cobimetinib, and Alectinib," *Org. Process Res. Dev.*, 20(11): 1855-1869 (2016).

Kinoshita et al., "Design and synthesis of a highly selective, orally active and potent anaplastic lymphoma kinase inhibitor (CH5424802)," *Bioorg. Med. Chem.*, 20(3): 1271-1280 (2012).

Kinoshita et al., "9-Substituted 6,6-Dimethyl-11-oxo-6,11-dihydro-5H-benzo[b]carbazoles as Highly Selective and Potent Anaplastic Lymphoma Kinase Inhibitors," *J. Med. Chem.*, 54(18): 6286-6294 (2011).

Leadbeater et al., "Rapid, easy copper-free Sonogashira couplings using aryl iodides and activated aryl bromides," *Tetrahedron Letters* 44: 8653-8656 (2003).

*Reaxys Database*, Elsevier Lif Sci IP Ltd, XP002784398, Accession No. 46135094 (Aug. 1, 2017)—1 pg.

European Patent Office, International Search Report in International Application No. PCT/IB2018/054932 (dated Jan. 2, 2019).

European Patent Office, Written Opinion in International Application No. PCT/IB2018/054932 (dated Jan. 2, 2019).

International Bureau of WIPO, International Preliminary Report on Patentability (Chapter 1) in International Application No. PCT/IB2018/054932 (dated Jan. 7, 2020).

European Patent Office, Extended European Search Report in European Patent Application No. 19 18 4409.1 (dated Sep. 12, 2019).

PROCESS FOR PREPARING ALECTINIB OR A PHARMACEUTICALLY ACCEPTABLE SALT THEREOF

CROSS-REFERENCE TO RELATED APPLICATIONS

This patent application is a divisional of co-pending U.S. patent application Ser. No. 16/627,160, filed on Dec. 27, 2019, which is the U.S. national stage of International Patent Application No. PCT/IB2018/054932, filed on Jul. 4, 2018, which claims the benefit of Indian Patent Application No. IN201711023632, filed Jul. 5, 2017, the disclosures of which are incorporated herein by reference in their entireties for all purposes.

FIELD OF THE INVENTION

The present invention relates to a process for preparing Alectinib or a pharmaceutically acceptable salt thereof. The present invention also relates to novel polymorphic forms of Alectinib and Alectinib hydrochloride.

BACKGROUND OF THE INVENTION

Alectinib, chemically known as 9-ethyl-6,6-dimethyl-8-(4-morpholin-4-yl -piperidin-1-yl)-11-oxo-6,11-dihydro-5H-benzo[b]carbazole-3-carbonitrile, is represented by formula I.

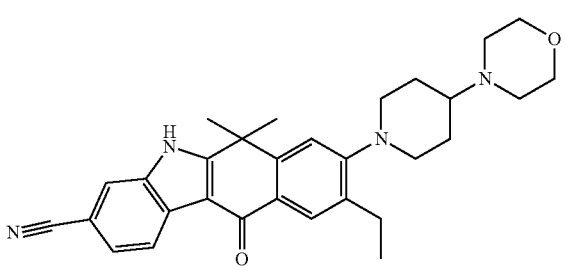

Formula I

Alectinib is approved as the hydrochloride salt, which is the active ingredient of drug Alecensa® and is intended for oral administration in the form of capsule. It is an anaplastic lymphoma kinase (ALK) inhibitor indicated for the treatment of patients with non-small-cell lung cancer (NSCLC).

Alectinib, as represented by formula I and its hydrochloride salt were described in WO2010/143664. Example 366 of this PCT application describes the preparation of Alectinib and its hydrochloride salt as depicted in scheme-1:

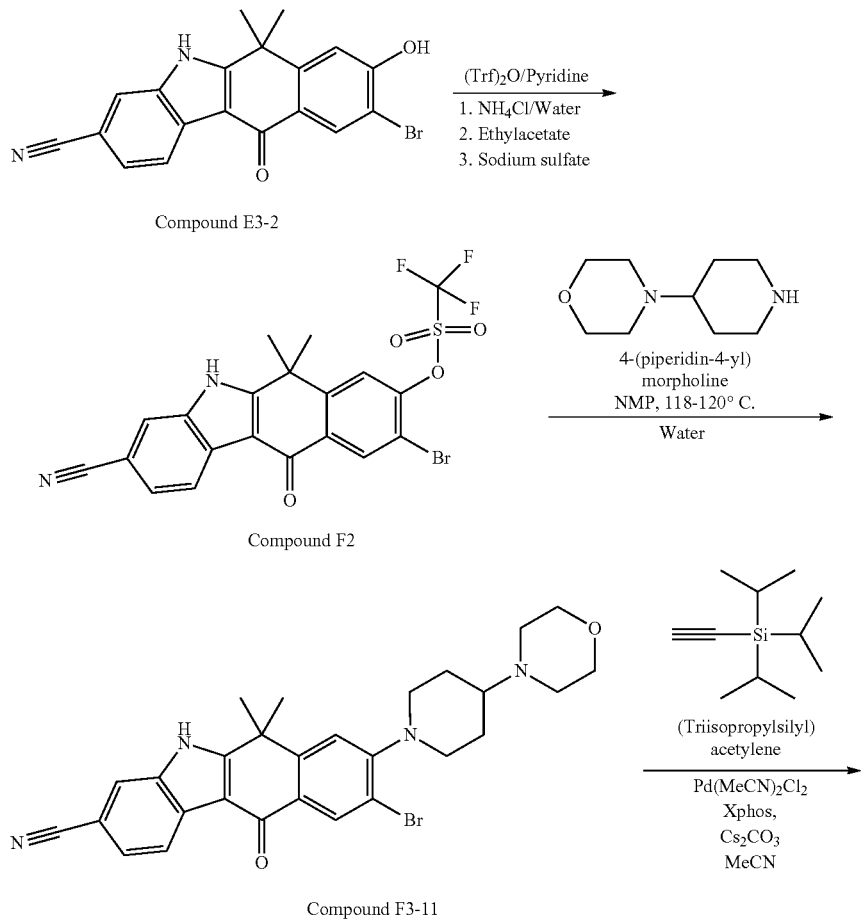

Scheme-1

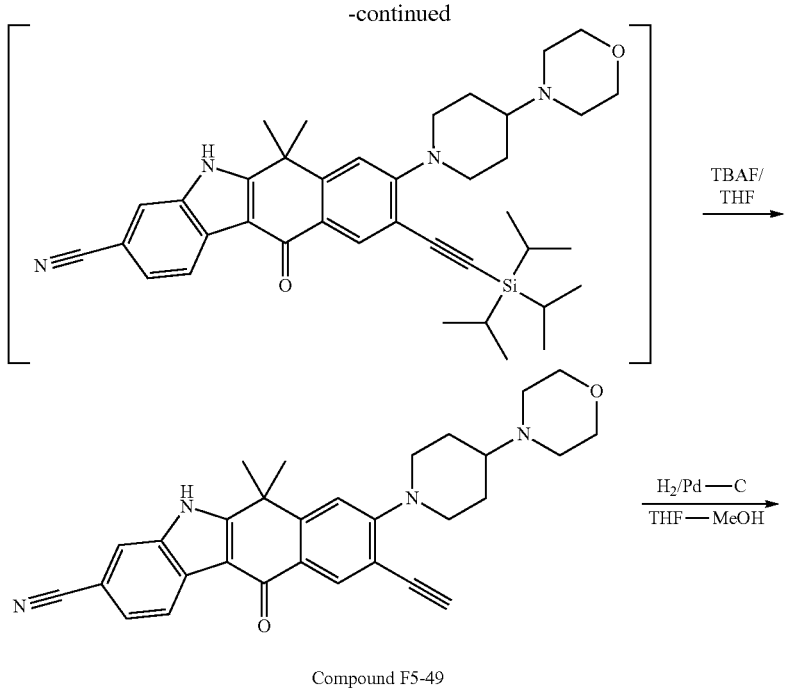

Compound F5-49

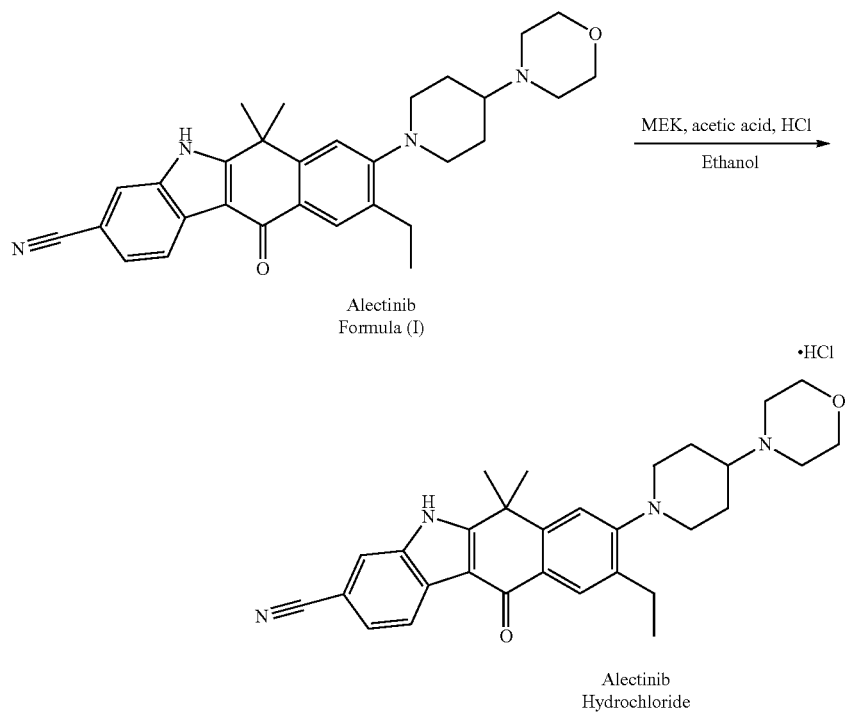

Alectinib
Formula (I)

Alectinib
Hydrochloride

Kinoshita et al., *Bioorg. Med. Chem.*, 2012, 20, 1271-1280 also describes the process for preparation of Alectinib using the above process.

In the above process, Alectinib hydrochloride was prepared starting from compound E3-2 using a six step process. Specifically, introduction of ethyl group in the compound F3-11 involves a three step process: first conversion of bromo group to triisopropylsilyl protected acetylene group, which is converted to ethynyl group and finally to ethyl group by catalytic hydrogenation. The above mentioned process has several disadvantages: lengthy process (six steps), the use of hydrogen gas and Pd/C catalysts and use of chromatographic techniques for the isolation/purification of intermediates. Further, the yield of Alectinib obtained by the process, as described above, is pretty low (approx. 8.8%). Also, use of chromatographic purification renders the above process not ideal for industrial production.

WO2010/143664 also discloses another process for preparation of Alectinib and its hydrochloride salt in Example 805, as depicted in scheme-2:

Scheme-2

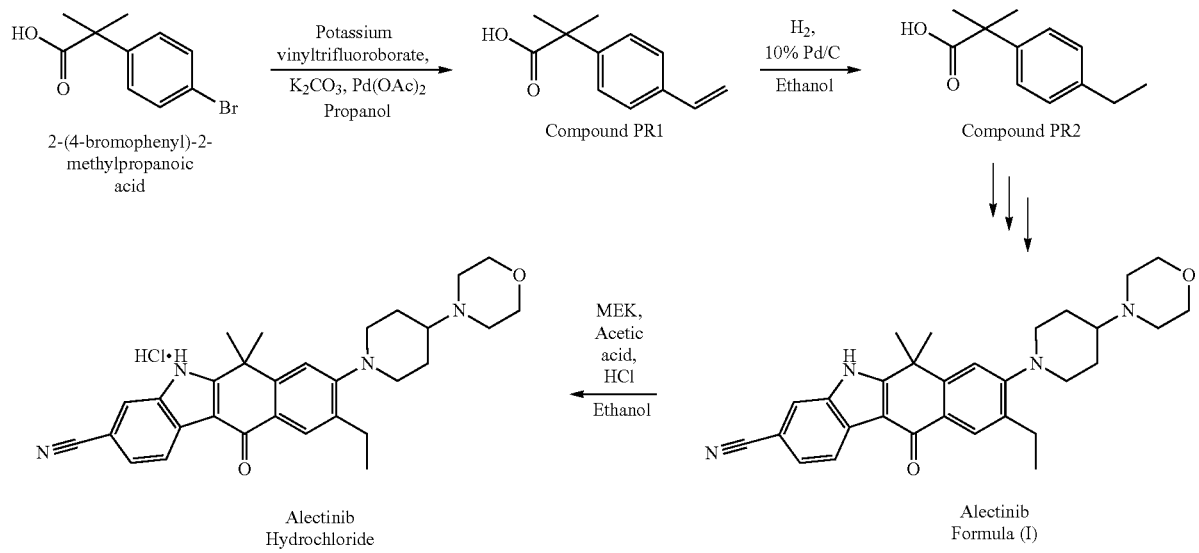

In the above process, Alectinib hydrochloride was prepared starting from 2-(4-bromophenyl)-2-methylpropanoic acid, using a ten step process. The process involves introduction of ethyl group in the starting compound by a two step process: first conversion of bromo group to vinyl group and then catalytic hydrogenation to ethyl group. The above mentioned process is also lengthy and involves use of hydrogen gas and Pd/C catalysts, which make the process less attractive for commercial manufacturing.

CN105777710 discloses a process for the preparation of Alectinib, as shown in scheme 3:

Scheme-3

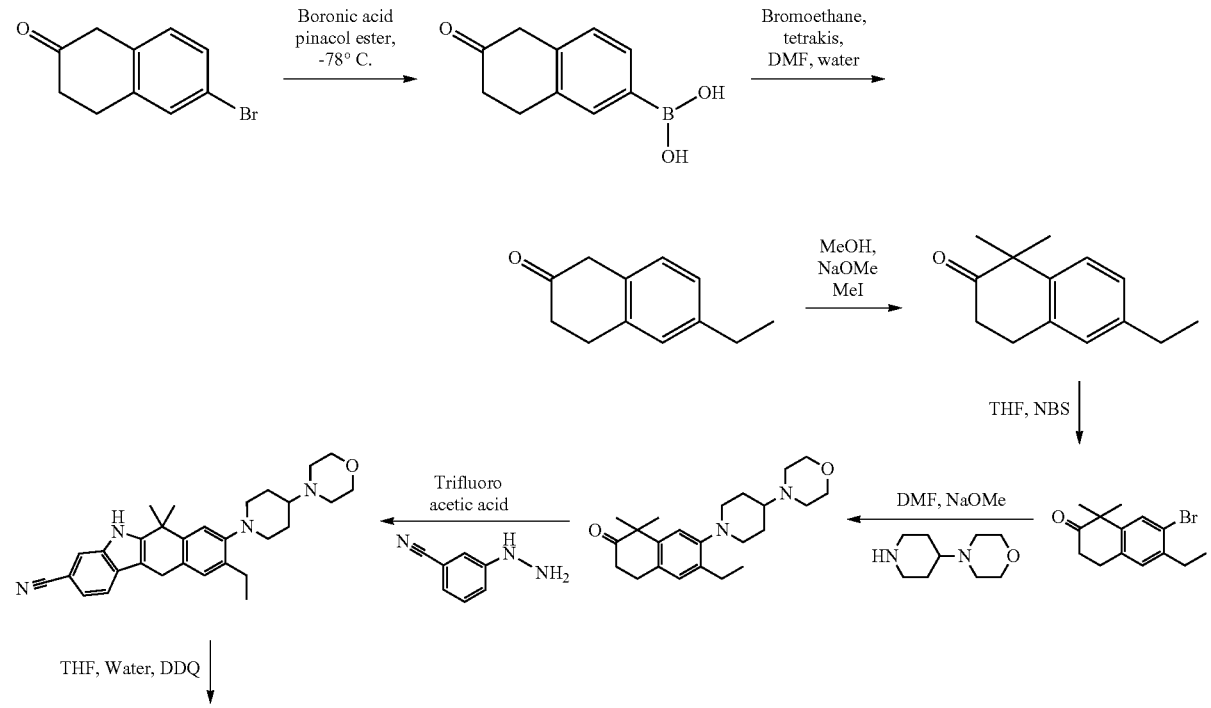

-continued

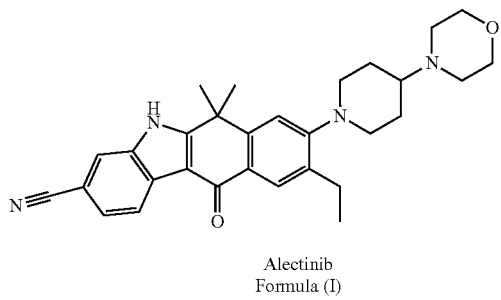

Alectinib
Formula (I)

This Chinese patent application describes preparation of Alectinib starting from 6-bromo-3,4-dihydro-2-naphthalenone using seven chemical steps. The process involves introduction of ethyl group in the starting compound by a two step process: first converting 6-bromo-3,4-dihydro-2-napthalenone to its boronic acid derivative, followed by catalytic coupling with bromoethane. The process requires that reaction mixture during boronization is maintained at −78° C. and this two step process takes long time, approx. 26 hours, to complete. The resulting compound is then converted to Alectinib using various reaction steps, which is purified by column chromatography. The use of low temperature condition, longer reaction time, chromatographic techniques and involvement of a larger number of reaction steps make this process less attractive from industrial point of view.

From the foregoing, it is apparent that the methods for the preparation of Alectinib or a pharmaceutically acceptable salt thereof reported so far suffer from one or more drawbacks, such as the extensive use of column chromatography, low yield, longer reaction time and a larger number of reaction steps, in particular with regard to the introduction of the ethyl group during the process, which requires two or more reaction steps.

Despite the existence of processes for the preparation of Alectinib or a pharmaceutically acceptable salt thereof, there still remains a need to develop an efficient, simple and industrially viable synthetic process, which can overcome the drawbacks of the prior art and would reduce the reaction time and the number of reaction steps. It is of particular importance to develop a method that would allow for the increase in yield for particular steps, which in turn would lead to an increase in the yield of the whole technology.

Further, the problem also lies with the solubility of Alectinib hydrochloride. It is insoluble in water across the whole pH range and in different solvents.

There are various routine techniques available in the art to enhance the solubility of poorly soluble drugs such as physical and chemical modifications of the drug e.g., particle size reduction, solid dispersion, use of surfactant and complexation. Selection of a solubility improving method depends on drug property, site of absorption and required dosage form characteristics. Polymorphic forms of drug can prove interesting for drug developers because their thermodynamic and physicochemical properties, such as energy, melting point, density, stability and in particular solubility, may offer an improvement over the original form. Crystalline polymorphs have the same chemical composition, but different internal crystal structures and therefore possess different physicochemical properties because of their different lattice structures and/or different molecular conformations.

Alectinib hydrochloride shows polymorphism and exists in different polymorphic forms.

European application EP3135671 relates to three crystalline forms of Alectinib hydrochloride namely type I, type II and type III. Example 2 of this patent application discloses that type II is not stable and tends to absorb moisture in high humidity to form a tetrahydrate and in low humidity; it tends to dehydrate to form anhydrate. Similarly, type III also converts to type II on drying.

WO2016/021707 discloses an amorphous form of Alectinib hydrochloride and a solid dispersion technique to overcome the solubility issue and to obtain sufficient bioavailability when administered orally. However, amorphous forms may be very difficult to purify since simple steps like crystallization normally do not work with the amorphous material.

In view of above, the polymorphic forms of Alectinib hydrochloride known in the prior art have either stability issues or have problem with simple purification.

Thus, there is a need for new polymorphic forms of Alectinib hydrochloride having desirable processing properties, such as ease of processing and ease of purification. New polymorphic forms and solvates of a pharmaceutically useful compound or salt thereof can also provide an opportunity to improve the performance characteristics of an active pharmaceutical ingredient (API). It may give advantage by providing a product with the better quality of final API in terms of purity and yield.

In order to overcome the problems associated with the prior art and to fulfill the need of the art, the inventors of the present invention have developed a process which provides Alectinib or pharmaceutically acceptable salt thereof in high yield using lesser reaction steps and also eliminating expensive and time-consuming column chromatography. Also, the present invention provides novel polymorphic forms of Alectinib and Alectinib hydrochloride that have advantageous properties.

OBJECT OF THE INVENTION

It is an objective of the present invention to overcome the drawbacks of the prior art as described above.

It is another objective of the present invention to provide an improved and industrially viable process for the synthesis of Alectinib or a pharmaceutically acceptable salt thereof, by involving lesser reaction steps.

It is yet another objective of the present invention to provide an improved and industrially viable process for the synthesis of Alectinib or a pharmaceutically acceptable salt thereof, without using chromatographic techniques.

It is a further objective of the present invention to provide a process for the preparation of pharmaceutically acceptable salt of Alectinib, preferably Alectinib hydrochloride.

It is another objective of the present invention to provide novel polymorphic forms of Alectinib and Alectinib hydrochloride.

It is yet another objective of the present invention to provide processes for the preparation of novel polymorphic forms of Alectinib and Alectinib hydrochloride.

SUMMARY OF THE INVENTION

The inventors of present invention have developed a process for preparing Alectinib of formula I,

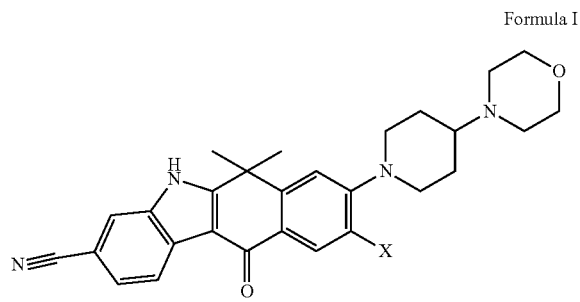

Formula I or a pharmaceutically acceptable salt thereof. Compared to the prior art processes, the process of the present invention may advantageously involve a reduced number of reaction steps and may advantageously provide the final product in higher yields. Preferably, the present invention provides a process for preparing Alectinib of formula I or a pharmaceutically acceptable salt thereof, wherein the ethyl group present in formula I is introduced in a single step.

In a first aspect, the present invention provides a process for preparing Alectinib of formula I or a pharmaceutically acceptable salt thereof, comprising the reaction of a compound of formula II,

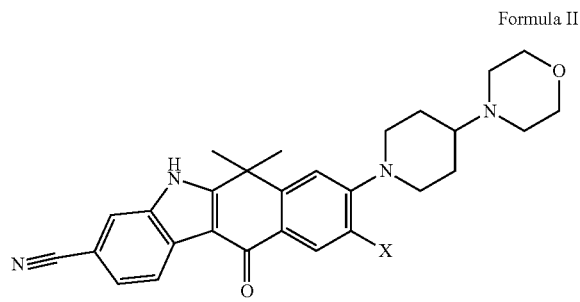

Formula II wherein X is halo, with diethylzinc.

In a second aspect, the present invention provides a crystalline form B of Alectinib characterized by an X-ray powder diffraction (XRPD) pattern comprising peaks at about 10.6 and 12.6±0.2° 2θ.

In a third aspect, the present invention provides a process for preparing the crystalline form B of Alectinib, comprising the steps of:
  a) contacting Alectinib with a solvent selected from the group consisting of alcohols, halogenated solvents or mixture thereof; and
  b) isolating the crystalline form B of Alectinib.

In a fourth aspect, the present invention provides a process for preparing Alectinib hydrochloride, comprising the steps of:

a) contacting Alectinib with a solvent;
  b) adding hydrochloric acid to the reaction mixture of step a); and
  c) isolating Alectinib hydrochloride.

In a fifth aspect, the present invention provides a process for preparing type I of Alectinib hydrochloride, wherein in step a) of the above process (i.e., the process according to the fourth aspect), the solvent is selected from the group consisting of alcohols, halogenated solvents or mixture thereof.

In a sixth aspect, the present invention provides a crystalline form IV of Alectinib hydrochloride, characterized by an X-ray powder diffraction (XRPD) pattern comprising peaks at about 5.5, 16.0 and 19.9±0.2° 2θ.

In a seventh aspect, the present invention provides a process preparing the crystalline form IV of Alectinib hydrochloride, comprising the steps of:
  a) contacting Alectinib with acetone;
  b) adding hydrochloric acid to the reaction mixture of step a); and
  c) isolating the crystalline form IV of Alectinib hydrochloride.

In an eighth aspect, the present invention provides a crystalline form V of Alectinib hydrochloride, characterized by an X-ray powder diffraction (XRPD) pattern comprising peaks at about 14.3, 20.0, 21.7 and 25.0±0.2° 2θ.

In a ninth aspect, the present invention provides a process for preparing the crystalline form V of Alectinib hydrochloride, comprising the steps of:
  a) contacting Alectinib with ethyl acetate;
  b) adding hydrochloric acid to the reaction mixture of step a); and
  c) isolating the crystalline form V of Alectinib hydrochloride.

In a tenth aspect, the present invention provides a crystalline form VI of Alectinib hydrochloride, characterized by an X-ray powder diffraction (XRPD) pattern comprising peaks at about 5.7, 14.8, 20.1 and 22.3±0.2° 2θ.

In an eleventh aspect, the present invention provides a process for preparing the crystalline form VI of Alectinib hydrochloride, comprising the steps of:
  a) contacting Alectinib with acetonitrile;
  b) adding hydrochloric acid to the reaction mixture of step a); and
  c) isolating the crystalline form VI of Alectinib hydrochloride.

In a twelfth aspect, the present invention provides a pharmaceutical composition comprising Alectinib or a pharmaceutically acceptable salt thereof prepared by the process of the present invention and at least one pharmaceutically acceptable excipient.

In a thirteenth aspect, the present invention provides a pharmaceutical composition comprising a crystalline form of Alectinib hydrochloride selected from crystalline form IV, form V, form VI of Alectinib hydrochloride or a mixture thereof and at least one pharmaceutically acceptable excipient.

In a fourteenth aspect, the present invention provides a method of treating cancer, comprising administering a therapeutically effective amount of Alectinib or a pharmaceutically acceptable salt thereof prepared by the process of the present invention.

In a fifteenth aspect, the present invention provides a method of treating cancer, comprising administering a therapeutically effective amount of a crystalline form of Alectinib hydrochloride selected from crystalline form IV, form V, form VI of Alectinib hydrochloride or a mixture thereof.

In a sixteenth aspect, the present invention provides a method of preparing a pharmaceutical composition, comprising a step of admixing a crystalline form of Alectinib hydrochloride selected from crystalline form IV, form V, form VI of Alectinib hydrochloride or a mixture thereof with one or more pharmaceutically acceptable excipients.

Definitions

The following definitions are used in connection with the present application, unless it is indicated otherwise.

The term "ambient temperature" refers to a temperature ranging from about 15° C. to 35° C., preferably to a temperature ranging from about 20° C. to 30° C., more preferably to a temperature of 25° C.

The terms "comprising" and "comprises" mean the elements recited, or their equivalents in structure or function, plus any other element or elements which are not recited.

The terms "having" and "including" are also to be construed as open ended. All ranges recited herein include the endpoints, including those that recite a range between two values. Whether so indicated or not, all values recited herein are approximate as defined by the circumstances, including the degree of expected experimental error, technique error, and instrument error for a given technique used to measure a value.

The term "optional" or "optionally" is taken to mean that the event or circumstance described in the specification may or may not occur, and that the description includes instances where the event occurs and instances where it does not.

As used herein, the term "contacting" includes mixing, adding, slurring, stirring or a combination thereof.

As used herein, the terms "about" are to be construed as modifying a term or value such that it is not an absolute. Such terms will be defined by the circumstances. This includes, at the very least, the degree of expected experimental error, technique error and instrument error for a given technique used to measure a value.

The term "substantially the same" with reference to analytical characterization such as X-ray powder diffraction (XRPD) peak positions means that typical peak position and intensity variability are taken into account. For example, one skilled in the art will appreciate that the peak positions (2 theta) will show some inter-apparatus variability, typically as much as 0.2°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only.

As used herein, the term "solvate" refers to the crystalline solid adducts containing either stoichiometric or nonstoichiometric amounts of a solvent incorporated within the crystal structure.

The term "pharmaceutically acceptable salts", includes salts with an inorganic acid e.g., hydrochloric acid, hydroiodic acid, phosphoric acid, phosphonic acid, sulfuric acid, hydrobromic acid or an organic acid, e.g., a carboxylic acid such as formic acid, acetic acid, citric acid, malic acid, maleic acid, tartaric acid, succinic acid, salicylic acid, trifluoroacetic acid, trichloroacetic acid, oxalic acid, benzoic acid or a sulfonic acid such as p-toluene sulfonic acid or methanesulfonic acid.

Abbreviations

XRPD X-ray powder diffraction
TGA Thermal gravimetric analysis
$^{13}$C-NMR Carbon-13 nuclear magnetic resonance
IR Infrared spectroscopy
HPLC High Performance Liquid Chromatography

DETAILED DESCRIPTION OF THE INVENTION

Figure 1:
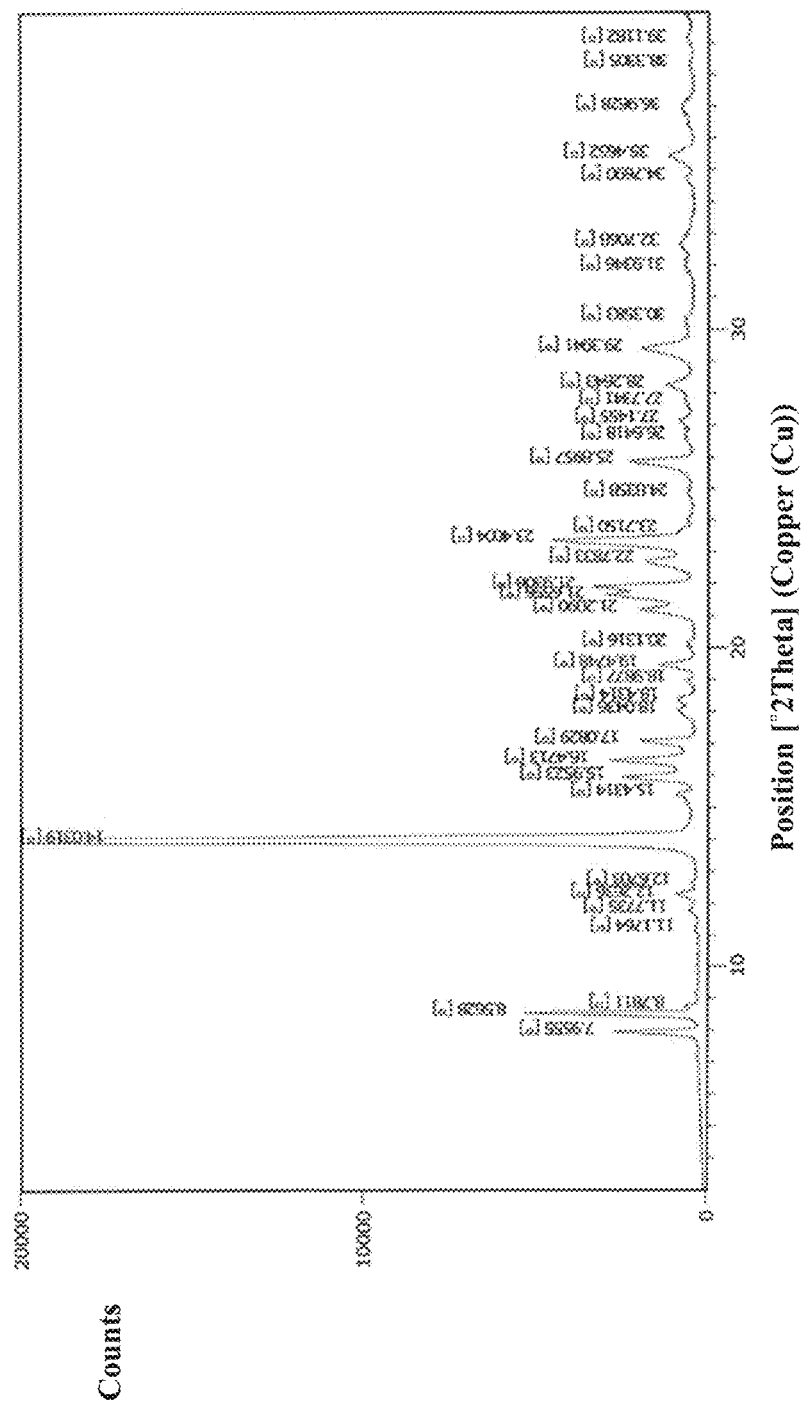
FIG. 1; represents an X-ray powder diffraction (XRPD) pattern of the crystalline form A of Alectinib, obtained as per reference Example-1.

The present invention provides an improved and industrially viable process for preparing Alectinib or a pharmaceutically acceptable salt thereof, in particular Alectinib hydrochloride. Further, the present invention provides novel polymorphic forms of Alectinib and Alectinib hydrochloride.

In a first aspect, the present invention provides a process for preparing Alectinib of formula I,

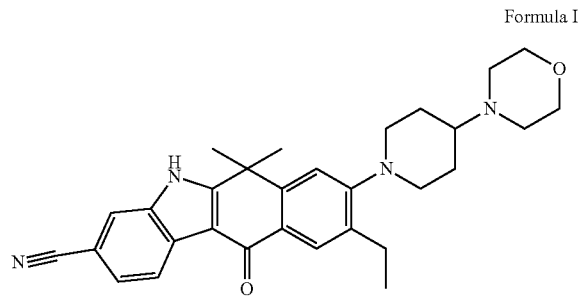 [SMILES: CCc1cc2c(cc1N1CCC(N3CCOCC3)CC1)C(C)(C)c1[nH]c3cc(C#N)ccc3c1C2=O]

Formula I or a pharmaceutically acceptable salt thereof, comprising the reaction of a compound of formula II,

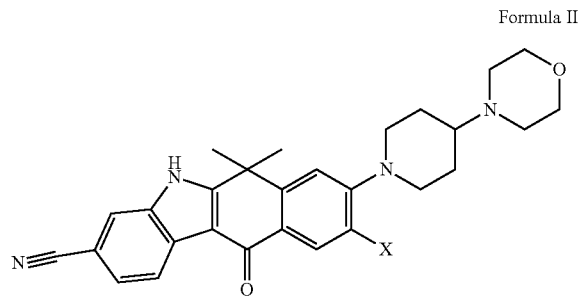

Formula II wherein X is halo,
with diethylzinc.

Preferably, X is fluoro, chloro, bromo or iodo. More preferably, X is fluoro, chloro or bromo. Also more preferably, X is chloro, bromo or iodo. Even more preferably, X is chloro or bromo. Also even more preferably, X is bromo or iodo. Particularly preferably, X is bromo.

Preferably, the reaction is carried out in the presence of a catalyst.

More preferably, the reaction is carried out in the presence of a catalyst and a ligand.

Preferably, the catalyst is a palladium (II) catalyst. Preferably, the palladium (II) catalyst is selected from the group consisting of palladium(II) acetate, [1,2-bis(diphenylphosphino)ethane]dichloropalladium(II) and [1,1'-bis(diphenylphosphino) ferrocene]palladium(II) dichloride. Particularly preferably, the palladium (II) catalyst is palladium(II) acetate.

Preferably, the reaction is carried out in the presence of palladium(II) acetate, [1,2-bis(diphenylphosphino)ethane] dichloropalladium(II) or [1,1'-bis(diphenylphosphino) ferrocene]palladium(II) dichloride. Particularly preferably, the reaction is carried out in the presence of palladium(II) acetate.

If present, the catalyst is preferably used in an amount in the range of from 1 to 30 mol %, more preferably 5 to 20 mol %, even more preferably 7 to 15 mol %, particularly preferably 8 to 12 mol %, with respect to the compound of formula II.

Preferably, the reaction is carried out in the presence of a ligand. Preferably, the ligand is a phosphine ligand. Preferably, the phosphine ligand is selected from the group consisting of tricyclohexylphosphine, tri-tert-butylphosphine, triphenylphosphine and 2-dicyclohexylphosphino-2',4',6'-triisopropylbiphenyl. Particularly preferably, the phosphine ligand is tricyclohexylphosphine.

Preferably, the reaction is carried out in the presence of tricyclohexylphosphine, tri-tert-butylphosphine, triphenylphosphine or 2-dicyclohexylphosphino-2',4',6'-triisopropylbiphenyl. Particularly preferably, the reaction is carried out in the presence of tricyclohexylphosphine.

If present, the ligand is preferably used in an amount in the range of from 5 to 40 mol %, more preferably 10 to 30 mol %, even more preferably 15 to 25 mol %, particularly preferably 18 to 22 mol %, with respect to the compound of formula II.

Diethylzinc used in the reaction may be availed commercially or may be generated in-situ by the reaction of ethyl magnesium bromide and zinc halide.

The molar ratio of diethylzinc to the compound of formula II is preferably in the range from 1:1 to 4:1, more preferably from 1.2:1 to 3:1, even more preferably from 1.5:1 to 2.5:1.

The reaction of the compound of formula II with diethylzinc may optionally be carried out in the presence of a solvent.

Preferably, the solvent is selected from the group consisting of amide solvents, sulfoxide solvents, ethers or mixture thereof. More preferably, the solvent is selected from the group consisting of N-methylpyrrolidone, dimethylsulfoxide, dimethylacetamide, diethylacetamide, dimethylformamide, dioxane, tetrahydrofuran or mixtures thereof. More preferably, the solvent is selected from dimethylacetamide, diethylacetamide or mixtures thereof. Particularly preferably, the solvent is dimethylacetamide.

The reaction of the compound of formula II with diethylzinc is preferably carried out at 0 to 80° C., more preferably 20 to 60° C., even more preferably 35 to 50° C., particularly preferably 40 to 45° C.

Alectinib thus obtained may be isolated by methods such as precipitation, cooling, filtration, centrifugation or combination thereof followed by optional washing with the water, solvent, a mixture of solvents or a mixture of solvent and water, or may be used directly for the preparation of pharmaceutically acceptable salts thereof.

Alectinib of formula I obtained by the process of present invention may optionally be purified by contacting Alectinib with a solvent or a solvent mixture. Preferably, the solvents is selected from the group consisting of water; halogenated solvents such as dichloromethane, dichloroethane, chloroform; alcohols such as methanol, ethanol, propanol, isopropanol, isobutanol; or mixture thereof. More preferably, Alectinib is purified with alcoholic solvent or a mixture of halogenated and alcoholic solvents. Most preferably, Alectinib is purified with methanol or a mixture of dichloromethane and methanol.

The Alectinib obtained by the process of present invention, with or without purification, is optionally dried by the methods such as vacuum drying, heat drying, spray drying, freeze drying, supercritical drying or natural air drying. Any of the mentioned methods may also be used in combination to ensure removal of unbound solvent. Preferably the Alectinib is dried by vacuum drying method. As will be recognized, the drying time will be dependent upon, amongst other things, the amount of material to be dried, and the particular drying method used. Generally a drying time of 30 minutes to 20 hours, preferably 1 to 18 hours, most preferably Alectinib is dried for 3 to 16 hours. Conveniently the drying is performed under vacuum and optionally under inert atmosphere, for example by passing a stream of warm inert gas such as nitrogen over or through the material.

The process described above may be varied, for example in terms of the quantity of the starting compound of formula II that is treated, the volume of the solvent or a mixture of solvents, the temperature of the treatment, cooling phases and/or drying conditions.

The inventors of the present invention have found that the process of the present invention provides Alectinib of formula I in higher yield as compared to processes known in the art. The method for the preparation of Alectinib of formula I, reported in prior arts (WO2010/143664, *Bioorg. Med. Chem.*, 2012, 20, 1271-1280), involves the use of tedious purification techniques such as flash or column chromatography and final product is obtained with an overall yield of approximately 8.8% which is too low to be commercially attractive.

Comparison of prior arts and present invention in terms of yield of Alectinib is shown in the following table:

| Process/reference | % Yield |
| --- | --- |
| *Bioorg. Med. Chem.*, 2012, 20, 1271-1280, as calculated | 8.8% |
| Reference Example 1 (repetition of prior art process) | 13.5% |
| Process of present invention | 51% |

From the above, it is evident that the process of the present invention provides Alectinib in high overall yield as compared to processes known in the art. The process of present invention typically provides Alectinib with more than 40% yield, preferably more than 45% yield, more preferably more than 50% yield. Also, the process of present invention provides several other advantages such as avoiding the use of tedious purification processes such as column/flash chromatography and less number of reaction steps, thereby drastically reducing the time for commercial manufacturing.

Further, it was found by the inventors that Alectinib isolated by the prior art methods (column chromatography using dichloromethane and methanol) displays X-ray powder diffraction (XRPD) pattern as shown in FIG. 1 and herein referred as "form A" of Alectinib. However, this process is not satisfactory on a commercial scale as it requires isolation of the product by column chromatography. Thus, inventors of present invention have developed a process that avoid column chromatography and result in a new crystalline form of Alectinib, which is described herein as crystalline "form B" of Alectinib.

In a second aspect, the present invention provides a crystalline form B of Alectinib.

Figure 2:
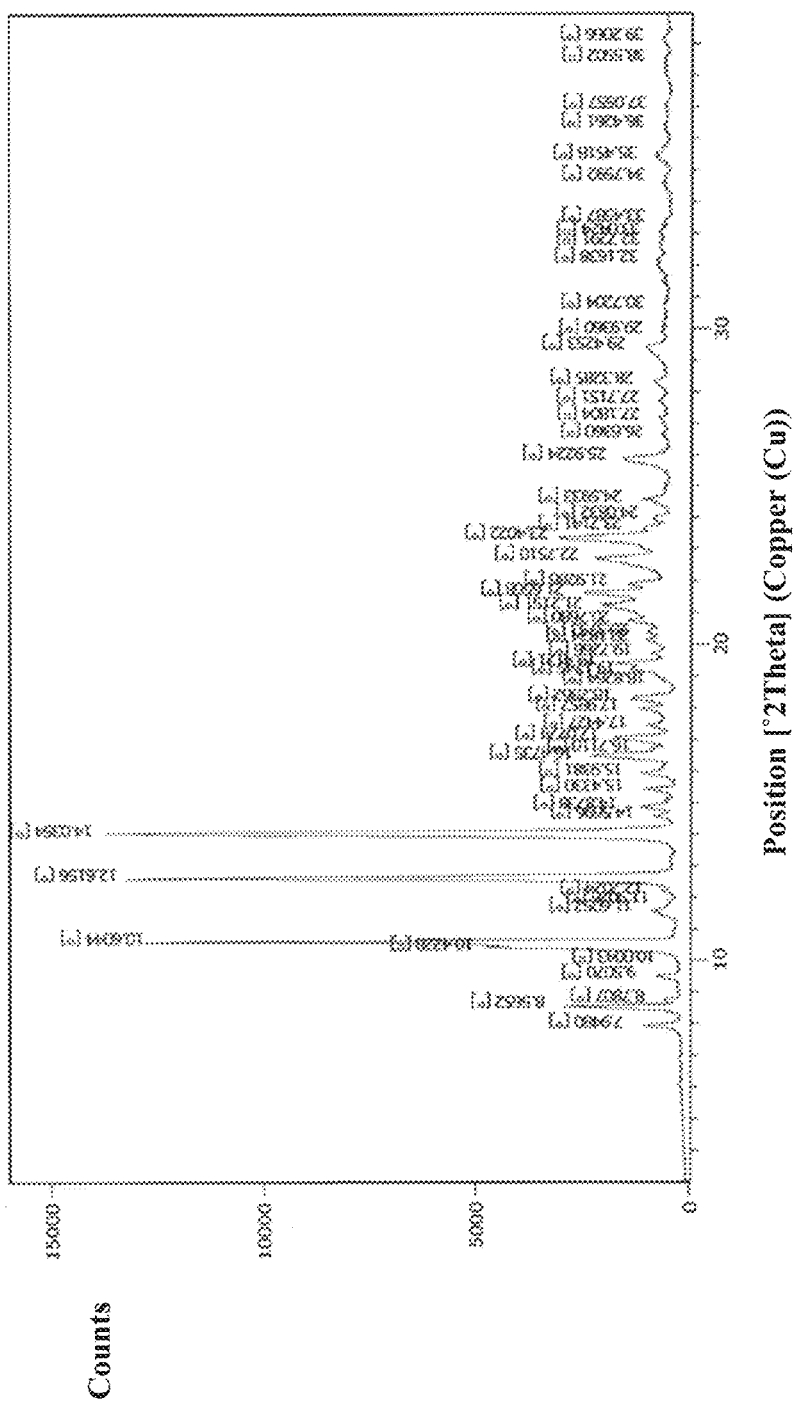
FIG. 2; represents an X-ray powder diffraction (XRPD) pattern of the crystalline form B of Alectinib of the present invention.

The crystalline form B of Alectinib is characterized by an X-ray powder diffraction (XRPD) pattern comprising peaks at about 10.6 and 12.6±0.2° 2θ. The crystalline form B of Alectinib is characterized by an X-ray powder diffraction (XRPD) pattern further comprising peaks at about 8.6, 14.0, 21.7, 22.8 and 23.4±0.2° 2θ. The crystalline form B of Alectinib is characterized by an X-ray powder diffraction (XRPD) pattern substantially the same as depicted in FIG. 2.

In a third aspect, the present invention provides a process for preparing the crystalline form B of Alectinib comprising the steps of:
 a) contacting Alectinib with a solvent selected from the group consisting of alcohols, halogenated solvents or mixture thereof; and
 b) isolating the crystalline form B of Alectinib.

The solvent in the step a) is preferably selected from alcohols such as methanol, ethanol, propanol or isopropanol; halogenated solvents such as dichloromethane or dichloroethane, chloroform; or a mixture thereof; preferably the solvents in step a) is a mixture of halogenated and alcoholic solvents; more preferably a mixture of dichloromethane and methanol. Step a) may be carried out at 15° C. to 80° C.; preferably at ambient temperature. The reaction mixture is optionally treated with activated carbon.

The crystalline form B of Alectinib thus obtained may be isolated by methods such as distillation, precipitation, cooling, filtration, centrifugation or combination thereof followed by optional washing with a pre-cooled solvent or a mixture of solvents. Preferably the crystalline form B of Alectinib may be isolated by cooling the reaction mixture at ambient temperature and may further cool down to −5° C. to 15° C., preferably at 0 to 5° C.

The crystalline form B of Alectinib obtained by the process of present invention, is optionally dried by the methods such as vacuum drying, heat drying, spray drying, freeze drying, supercritical drying or natural air drying. Any of the mentioned methods may also be used in combination to ensure removal of unbound solvent. Preferably the crystalline form B of Alectinib is dried by vacuum drying method. As will be recognized, the drying time will be dependent upon, amongst other things, the amount of material to be dried, and the particular drying method used. Generally a drying time of 30 minutes to 20 hours, preferably 1 to 18 hours, most preferably the crystalline form B of Alectinib is dried for 3 to 16 hours. Conveniently the drying is performed under vacuum and optionally under inert atmosphere, for example by passing a stream of warm inert gas such as nitrogen over or through the material.

The crystalline form B of Alectinib obtained by the process of present invention is optionally converted to the pharmaceutically acceptable salt thereof.

The pharmaceutically acceptable salt of Alectinib can be prepared by treating the Alectinib with a suitable acid. The acid may be selected from an inorganic acid e.g., hydrochloric acid, hydroiodic acid, phosphoric acid, phosphonic acid, sulfuric acid, hydrobromic acid or an organic acid, e.g., a carboxylic acid such as formic acid, acetic acid, citric acid, malic acid, maleic acid, tartaric acid, succinic acid, salicylic acid, trifluoroacetic acid, trichloroacetic acid, oxalic acid, benzoic acid or a sulfonic acid such as p-toluene sulfonic acid or methanesulfonic acid.

The salt formation reaction may be carried out in the presence of a polar or non polar solvent selected from the group consisting of alcohols such as methanol, ethanol, propanol or isopropanol; ketones such as acetone, diisopropyl ketone or methylisobutyl ketone, methyl ethyl ketone; halogenated solvents such as dichloromethane or dichloroethane; ethers such as tetrahydrofuran, 1,4-dioxane; esters such as ethylacetate, methylacetate or isopropyl acetate; or mixtures thereof. The pharmaceutically acceptable salt of Alectinib may be isolated using conventional methods such as filtration, centrifugation.

Preferably, Alectinib is converted to Alectinib hydrochloride.

In a fourth aspect, the present invention provides a process for preparing Alectinib hydrochloride, comprising the steps of:
 a) contacting Alectinib with a solvent;
 b) adding hydrochloric acid to the reaction mixture of step a); and
 c) isolating Alectinib hydrochloride.

The solvent used in step a) is preferably selected from the group consisting of alcohols, ketones, halogenated solvents, ethers, esters, nitriles or mixtures thereof, preferably the solvent is selected from the group consisting of methanol, ethanol, propanol, isopropanol, acetone, diisopropyl ketone, methylisobutyl ketone, methyl ethyl ketone, dichloromethane, dichloroethane, chloroform, tetrahydrofuran, 1,4-dioxane, ethylacetate, methylacetate, isopropyl acetate, acetonitrile or mixture thereof, more preferably solvent is selected from isopropanol, acetone, ethyl acetate, acetonitrile or a mixture of dichloromethane and methanol.

Step a) may be carried out at 15 to 80° C.; preferably at ambient temperature for 30 minutes to 12 hours, preferably for 1-3 hours.

Hydrochloric acid used in step b) may be added in form of concentrated solution, aqueous solution or in solution with a solvent, wherein solvent can be same or different as used in step a).

Alectinib hydrochloride thus obtained may be isolated by methods such as precipitation, cooling, filtration, centrifugation or combination thereof followed by optional washing it with the solvent or a mixture of solvents used during the process.

The Alectinib hydrochloride, thus obtained, is optionally dried by the methods such as vacuum drying, heat drying, spray drying, freeze drying, supercritical drying or natural air drying. Any of the mentioned methods may also be used in combination to ensure removal of unbound solvent. Preferably the Alectinib hydrochloride is dried by vacuum drying method. As will be recognized, the drying time will be dependent upon, amongst other things, the amount of material to be dried, and the particular drying method used. Generally a drying time of 30 minutes to 20 hours, preferably 3 to 18 hours is sufficient. Conveniently the drying is performed under vacuum and optionally under inert atmosphere, for example by passing a stream of warm inert gas such as nitrogen over or through the material.

The process described above may be varied, for example in terms of the quantity of the starting Alectinib that is treated, the volume of the solvent or a mixture of solvents, the temperature of the treatment, cooling phases and/or drying conditions.

In a fifth aspect, the present invention provides a process for preparing type I of Alectinib hydrochloride, wherein the solvent used in the step a) of above process is preferably selected from the group consisting of alcohols, halogenated solvent or mixture thereof. Preferably, the process involves contacting Alectinib with isopropanol or a mixture of dichloromethane and methanol followed by treatment with hydrochloric acid.

Type I of Alectinib hydrochloride may be isolated by methods such as precipitation, cooling, filtration, centrifugation or combination thereof followed by optional washing it with the solvent or a mixture of solvents used during the process.

Thus obtained type I of Alectinib hydrochloride is optionally dried by the methods such as vacuum drying, heat drying, spray drying, freeze drying, supercritical drying or natural air drying.

Figure 3:
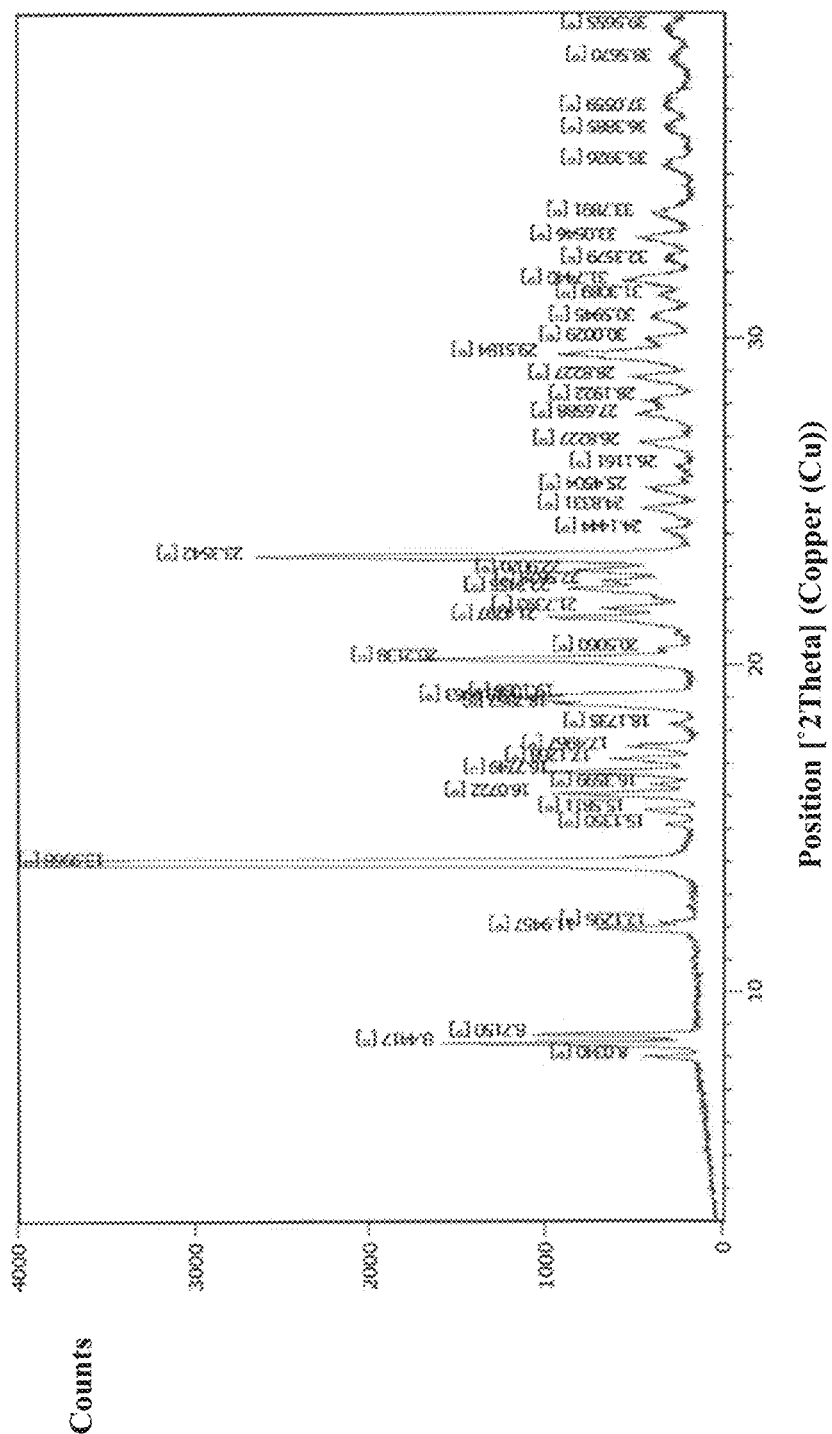
FIG. 3; represents an X-ray powder diffraction (XRPD) pattern of type I of Alectinib hydrochloride, obtained by the process of present invention.

The type I of Alectinib hydrochloride is characterized by X-ray powder diffraction (XRPD) pattern as depicted in FIG. 3.

The inventors of present invention found that Alectinib hydrochloride exists in different polymorphic forms when prepared using different solvent. Accordingly, the present invention also provides novel polymorphic forms of Alectinib hydrochloride, which may be characterized using various techniques. Examples of characterization methods include, but are not limited to, single crystal X-ray diffraction, X-ray powder diffraction (XRPD), simulated powder X-ray patterns, solid state $^{13}$C-NMR, Raman spectroscopy, infrared spectroscopy (IR), moisture sorption isotherms, thermal gravimetric analysis (TGA), differential scanning calorimetric (DSC) and hot stage techniques.

In aسixth aspect, the present invention provides a crystalline form IV of Alectinib hydrochloride.

Figure 4:
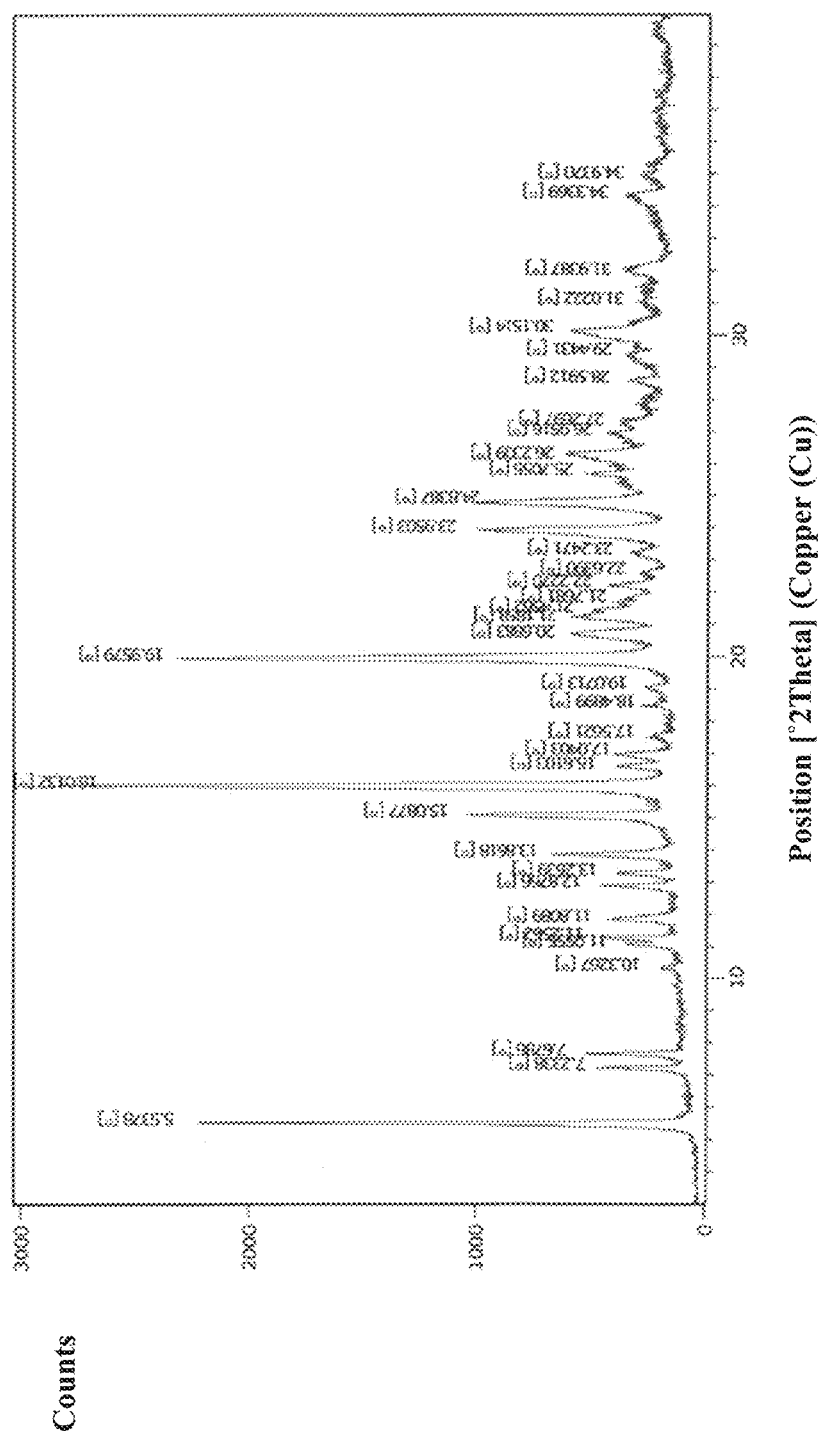
FIG. 4; represents an X-ray powder diffraction (XRPD) pattern of the crystalline form IV of Alectinib hydrochloride.

The crystalline Form IV of Alectinib hydrochloride is characterized by an X-ray powder diffraction (XRPD) pattern comprising peaks at about 5.5, 16.0 and 19.9±0.2° 2θ. The crystalline form IV of Alectinib hydrochloride may be characterized by an X-ray powder diffraction (XRPD) pattern further comprising peaks at about 13.9, 15.1, 23.9 and 24.8±0.2° 2θ. The crystalline Form IV of Alectinib hydrochloride may be characterized by an X-ray powder diffraction (XRPD) pattern substantially the same as depicted in FIG. 4.

The crystalline form IV of Alectinib hydrochloride is acetone solvate. The crystalline form IV of Alectinib hydrochloride contains about 2.5 to 3.5% by weight of Acetone.

Figure 5:
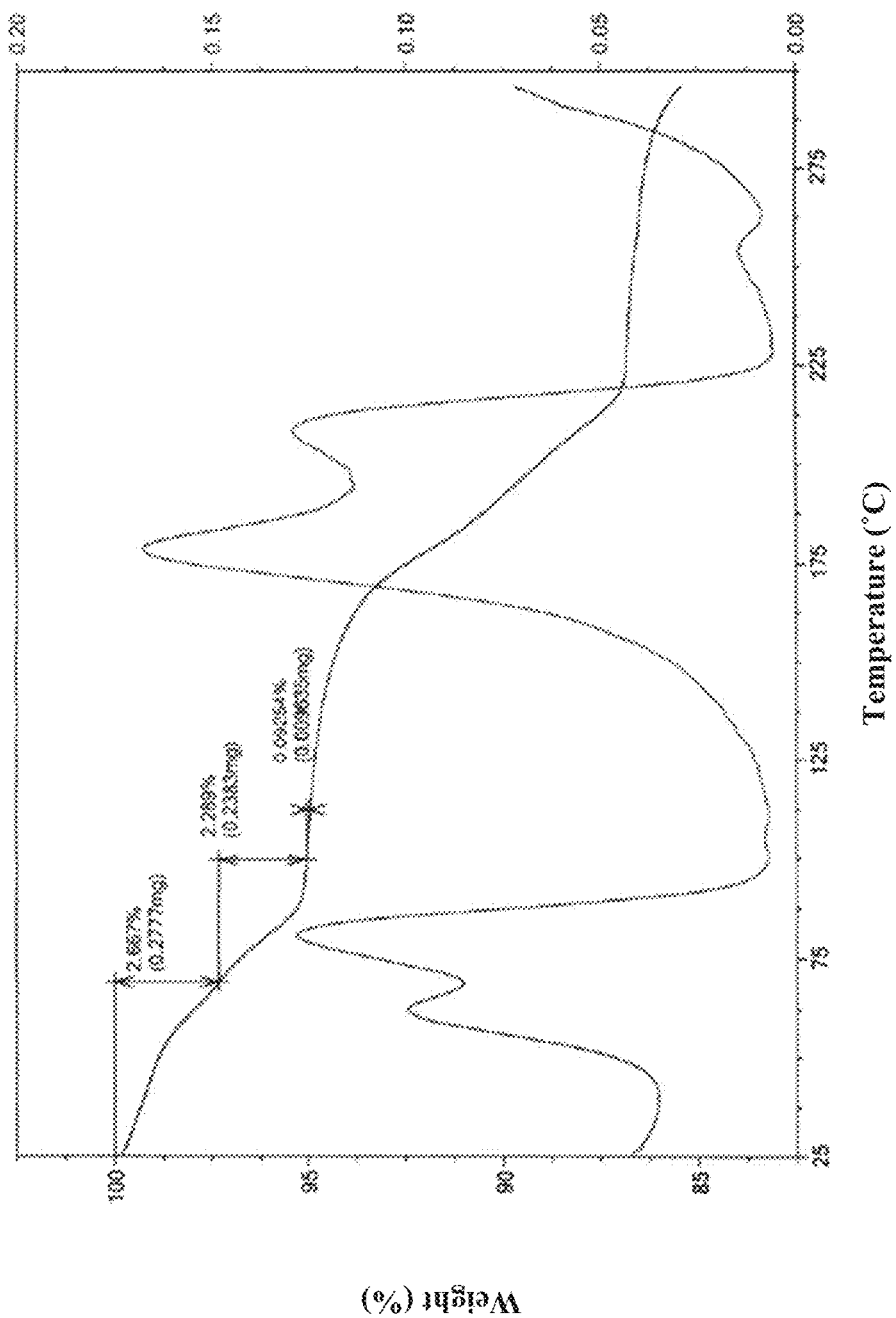
FIG. 5; represents a thermal gravimetric analysis (TGA) of the crystalline form IV of Alectinib hydrochloride.

The crystalline form IV of Alectinib hydrochloride may be further characterized by thermogravimetric analysis (TGA) as depicted in FIG. 5.

In a seventh aspect, the present invention provides a process for preparing the crystalline form IV of Alectinib hydrochloride, comprising the steps of:

a) contacting Alectinib with acetone;

b) adding hydrochloric acid to the reaction mixture of step a); and c) isolating the crystalline form IV of Alectinib hydrochloride.

The process of step a) may be carried out at 10 to 70° C.; preferably at 50 to 55° C.

The process of step b), wherein the hydrochloric acid may be added as aqueous solution or a solution in acetone; preferably aqueous solution of hydrochloric acid is added.

The reaction mixture obtained after step b) may be maintained at 15 to 80° C. for the time sufficient for the generation of crystalline form IV of Alectinib hydrochloride, followed by cooling at −5° C. to ambient temperature, preferably 0 to 10° C.

The crystalline form IV of Alectinib hydrochloride may be isolated by methods such as precipitation, cooling, filtration, centrifugation or combination thereof followed by optional washing it with the solvent or a mixture of solvents used during the process.

In an eighth aspect, the present invention provides crystalline form V of Alectinib hydrochloride.

Figure 6:
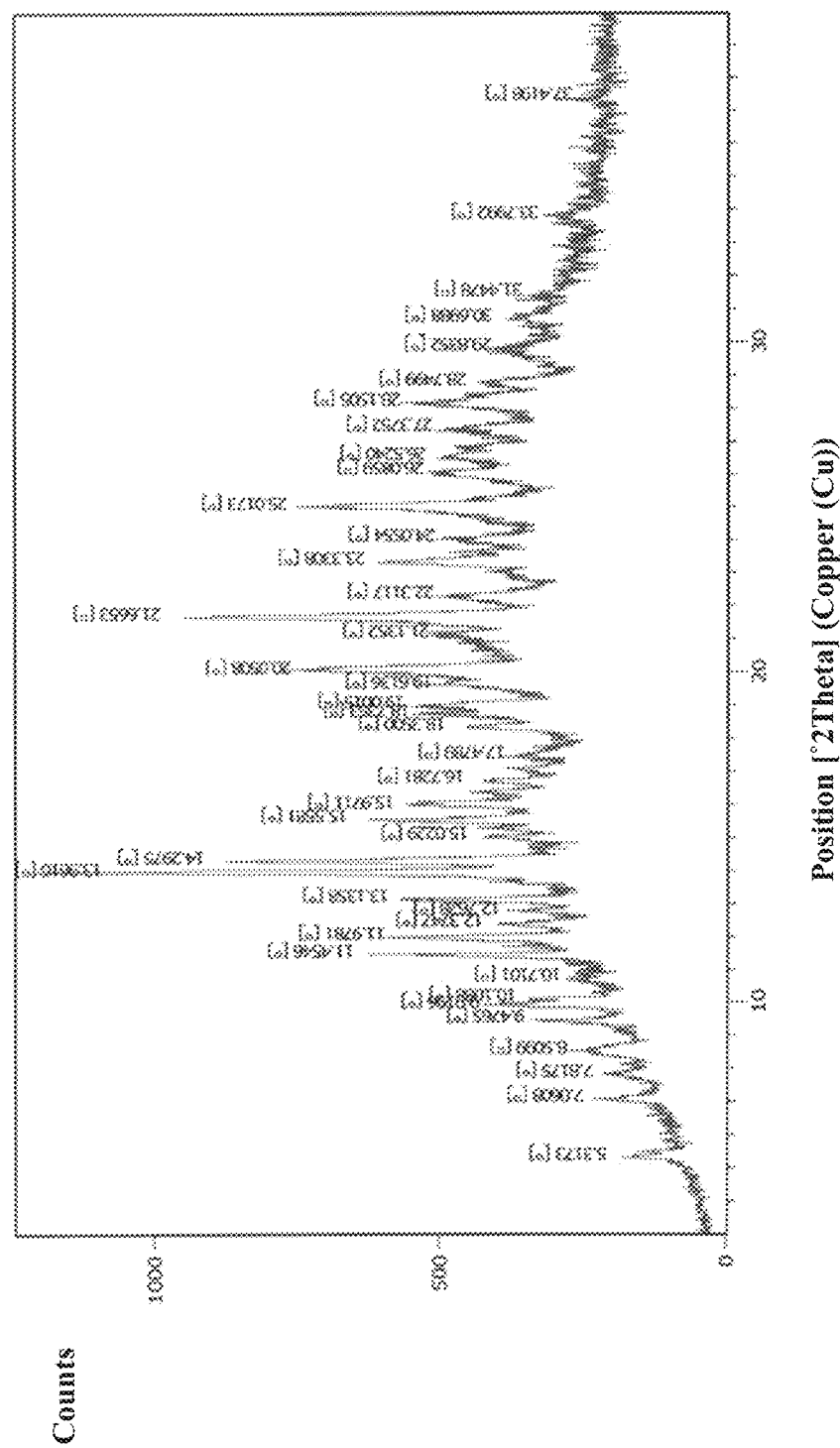
FIG. 6; represents an X-ray powder diffraction (XRPD) pattern of the crystalline form V of Alectinib hydrochloride.

The crystalline form V of Alectinib hydrochloride is characterized by an X-ray powder diffraction (XRPD) pattern comprising peaks at about 14.3, 20.0, 21.7 and 25.0±0.2° 2θ. The crystalline form V of Alectinib hydrochloride may be characterized by an X-ray powder diffraction (XRPD) pattern further comprising peaks at about 11.5, 12.0, 15.6 and 23.3±0.2° 2θ. The crystalline Form V of Alectinib hydrochloride may be characterized by an X-ray powder diffraction (XRPD) pattern substantially the same as depicted in FIG. 6.

In a ninth aspect, the present invention provides a process for preparing the crystalline form V of Alectinib hydrochloride, comprising the steps of:

a) contacting Alectinib with ethyl acetate;

b) adding hydrochloric acid to the reaction mixture of step a); and c) isolating the crystalline form V of Alectinib hydrochloride.

The process of step a) may be carried out at 20 to 80° C.; preferably at 50 to 70° C.

The process of step b), wherein the hydrochloric acid may be added as aqueous solution or a solution in ethyl acetate; preferably aqueous solution of hydrochloric acid is added.

The reaction mixture obtained after step b) may be maintained at 15 to 80° C. for the time sufficient for the generation of crystalline form V of Alectinib hydrochloride, followed by cooling at ambient temperature.

Crystalline form V of Alectinib hydrochloride may be isolated by methods such as precipitation, cooling, filtration, centrifugation or combination thereof followed by optional washing it with the solvent or a mixture of solvents used during the process.

In a tenth aspect, the present invention provides crystalline form VI of Alectinib hydrochloride.

Figure 7:
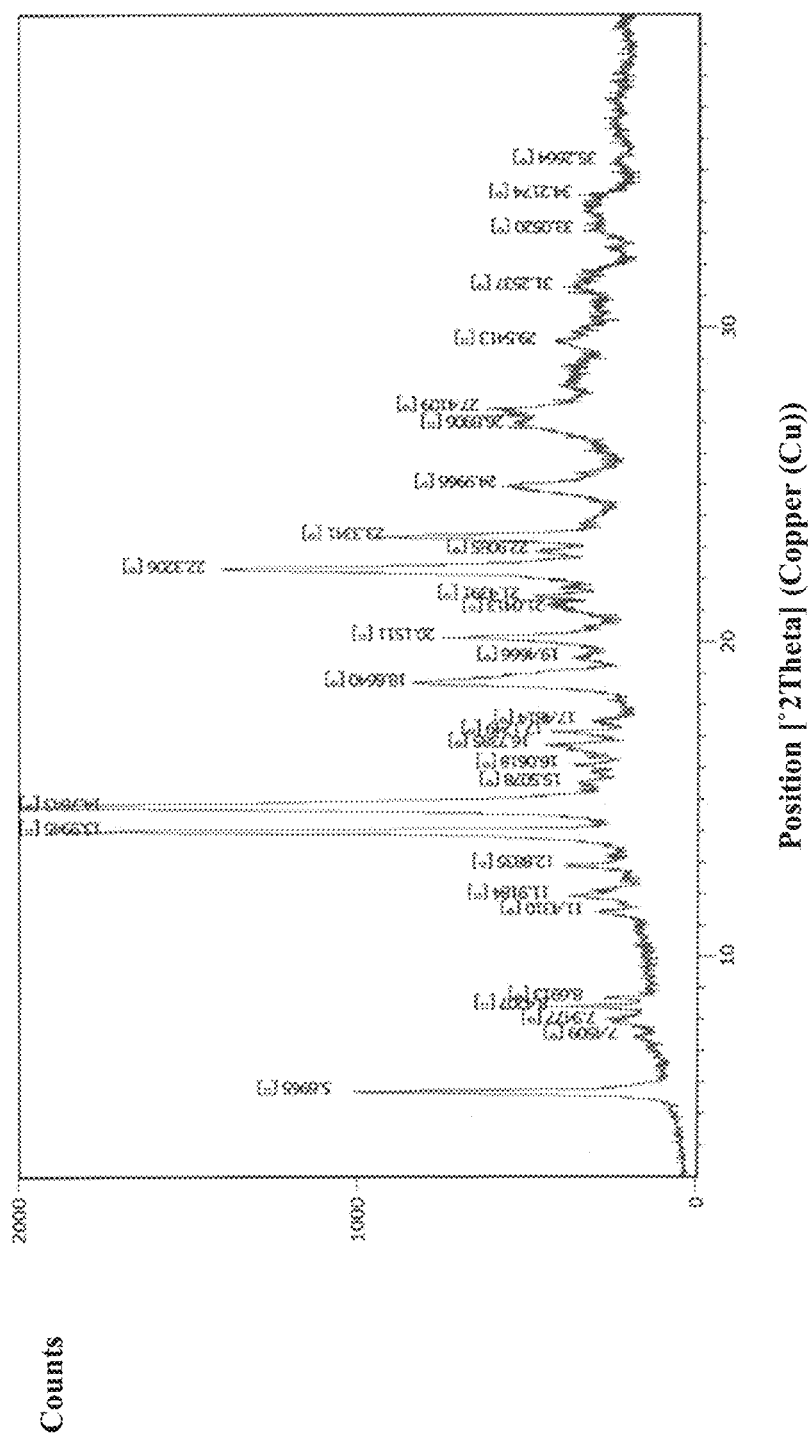
FIG. 7; represents an X-ray powder diffraction (XRPD) pattern of the crystalline form VI of Alectinib hydrochloride.

The crystalline form VI of Alectinib hydrochloride is characterized by an X-ray powder diffraction (XRPD) pattern comprising peaks at about 5.7, 14.8, 20.1 and 22.3±0.2° 2θ. The crystalline form VI of Alectinib hydrochloride may be characterized by an X-ray powder diffraction (XRPD) pattern further comprising peaks at about 18.7 and 23.3±0.2° 2θ. The crystalline Form VI of Alectinib hydrochloride may be characterized by an X-ray powder diffraction (XRPD) pattern substantially the same as depicted in FIG. 7.

In an eleventh aspect, the present invention provides a process for preparing the crystalline form VI of Alectinib hydrochloride, comprising the steps of:

a) contacting Alectinib with acetonitrile;

b) adding hydrochloric acid to the reaction mixture of step a); and c) isolating the crystalline form VI of Alectinib hydrochloride.

The process of step a) may be carried out at 20 to 75° C.; preferably at 50 to 70° C.

The process of step b), wherein the hydrochloric acid may be added as aqueous solution or a solution in acetonitrile; preferably aqueous solution of hydrochloric acid is added.

The reaction mixture obtained after step b) may be maintained at 15 to 80° C. for the time sufficient for the generation of crystalline form VI of Alectinib hydrochloride, followed by cooling at −5° C. to ambient temperature, preferably 0 to 10° C.

The crystalline form VI of Alectinib hydrochloride may be isolated by methods such as precipitation, cooling, filtration, centrifugation or combination thereof followed by optional washing it with the solvent or a mixture of solvents used during the process.

Thus obtained crystalline form IV, V or VI of Alectinib hydrochloride may be optionally dried by the methods such as vacuum drying, heat drying, spray drying, freeze drying, supercritical drying or natural air drying. Preferably the crystalline forms of Alectinib hydrochloride are dried by vacuum drying method. As will be recognized, the drying time will be dependent upon, amongst other things, the amount of material to be dried, and the particular drying method used. Generally a drying time of 30 minutes to 20 hours, preferably 3 to 16 hours is sufficient. Conveniently the drying is performed under vacuum and optionally under inert atmosphere, for example by passing a stream of warm inert gas such as nitrogen over or through the material.

The starting material, compound of formula II, used in the present invention, may be obtained by methods known in the art, e.g., as described in WO2010/143664 or *Bioorg. Med. Chem.*, 2012, 20, 1271-1280, preferably by the process described herein.

The present invention provides a process for preparing the compound of formula II, comprising the steps of:

a) contacting a compound of formula III

Formula III

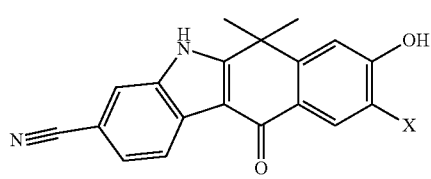

wherein, X is halo with a triflating agent and a base to give a compound of formula IV;

Formula IV

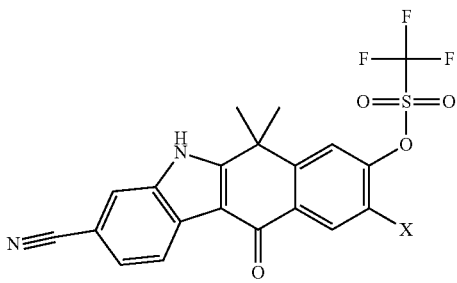

wherein, X is halo b) reacting the compound of formula IV with 4-(piperadine-4-yl-)-morpholine in a polar aprotic solvent; and c) isolating the compound of formula II.

The triflating agent used in step a) is preferably trifluoromethanesulfonyl chloride or trifluoromethanesulfonic anhydride, more preferably trifluoromethanesulfonic anhydride.

The base used in step a) is preferably an organic base selected from the group consisting of diisopropymethylamine, triethylamine, 4-dimethylaminopyridine, Imidazole and pyridine, preferably pyridine.

The reaction of step a) is optionally carried in the presence of an organic solvent selected from halogenated solvents such as chloroform, dichloromethane, tetrachloromethane or a mixture thereof; preferably dichloromethane.

The compound of formula IV, thus obtained may be isolated by methods such as precipitation, cooling, filtration, centrifugation or combination thereof followed by optional washing it with the solvent or a mixture of solvents or optional purification in a solvent or a mixture thereof. The solvent for the isolation/washing/purification may be selected from group consisting of water, hydrocarbon solvent such as hexane; ketonic solvent such as acetone or mixture thereof. Preferably the compound of formula IV is converted directly to the compound of formula II.

The polar aprotic solvent in step b) is preferably selected from the group consisting of amide solvents, sulfoxide solvents or mixture thereof. Preferably solvent is selected from the group consisting of N-methyl pyrrolidone, dimethylformamide, dimethylacetamide, dimethylsulfoxide or a mixture thereof; preferably the reaction is carried out in N-methyl pyrrolidone or dimethylacetamide.

The compound of formula II thus obtained may be isolated by methods such as precipitation, cooling, filtration, centrifugation or combination thereof followed by optional washing it with the solvent or a mixture of solvents, or can be used further directly for the preparation of Alectinib or a pharmaceutically acceptable salt thereof.

The compound of formula II, obtained by the process of present invention may optionally further be purified using a solvent or solvent mixture. The solvent for purification may be selected from group consisting of water, ketonic solvent such as acetone or mixture thereof.

The compound of formula II obtained by the process of present invention, with or without purification, is optionally dried by the methods such as vacuum drying, heat drying, spray drying, freeze drying, supercritical drying or natural air drying. Any of the mentioned methods may also be used in combination to ensure removal of unbound solvent. Preferably the compound of formula II is dried by vacuum drying method. As will be recognized, the drying time will be dependent upon, amongst other things, the amount of material to be dried, and the particular drying method used. Generally a drying time of 30 minutes to 20 hours, preferably 2 to 14 hours is sufficient. Conveniently the drying is performed under vacuum and optionally under inert atmosphere, for example by passing a stream of warm inert gas such as nitrogen over or through the material.

The process described above may be varied, for example in terms of the quantity of the starting compound of formula III or compound of formula IV that is treated, the volume of the solvent or a mixture of solvents, the temperature of the treatment, cooling phases and/or drying conditions.

In a twelfth aspect, the present invention provides a pharmaceutical composition comprising Alectinib or a pharmaceutically acceptable salt thereof, prepared by the process of present invention and at least one pharmaceutically acceptable excipient.

In a thirteenth aspect, the present invention provides a pharmaceutical composition comprising a crystalline form of Alectinib hydrochloride selected from crystalline form IV, form V, form VI of Alectinib hydrochloride or mixture thereof and at least one pharmaceutically acceptable excipient.

In a fourteenth aspect, the present invention provides a method of treating cancer, comprising administering a therapeutically effective amount of Alectinib or a pharmaceutically acceptable salt thereof, prepared by the process of present invention.

In a fifteenth aspect, the present invention provides a method of treating cancer, comprising administering a therapeutically effective amount of a crystalline form of Alectinib hydrochloride selected from crystalline form IV, form V, form VI of alectinib hydrochloride or mixture thereof.

In a sixteenth aspect, the present invention provides a method of preparing a pharmaceutical composition, comprising a step of admixing a crystalline form of Alectinib hydrochloride selected from crystalline form IV, form V, form VI of Alectinib hydrochloride or a mixture thereof with one or more pharmaceutically acceptable excipients.

The major advantage of the present invention is to obtain Alectinib or pharmaceutically acceptable salts thereof in high yield. The present invention employs less number of reaction steps, which noticeably enhances the yield of the obtained final product. Also, the present invention provides a simple process for the synthesis of Alectinib or a pharmaceutically acceptable salt thereof, resulting in a high yield, high purity and avoids chromatographic purification. Additionally, the present invention provides a new crystalline form of Alectinib free base and new crystalline forms of Alectinib hydrochloride.

Instrument

XRPD: X-ray diffraction data is obtained using a Bruker AXS D8 advance powder X-ray diffractometer, CuKα radiation, wavelength 1.54 Å.

TGA: TGA measurement is performed using a TGA Q500 V20, temperature range 25-300° C. and 10° C./min.

EXAMPLES

Detailed experimental parameters suitable for the preparation of Alectinib or pharmaceutically acceptable salts thereof according to the present invention are provided by the following examples, which are intended to be illustrative and not limiting.

Reference Example-1: Preparation of Alectinib (WO2010/143664, Bioorg. Med. Chem., 2012, 20, 1271-1280)

Step I: Preparation of 9-bromo-3-cyano-6,6-dimethyl-11-oxo-6,11-dihydro -5H-benzo[b]carbazole-8-yl-trifluoromethanesulfonate 9-Bromo-8-hydroxy-6,6-dimethyl-11-oxo-6,11-dihydro-5H-benzo[b]-carbazole-3-carbonitrile (2.0 g) and pyridine (30.0 mL) was stirred and cooled to 0-5° C. Trifluoromethanesulfonic anhydride (4.44 g) was added to the reaction mass and stirred at 20-25° C. followed by quenching with aq. ammonium chloride (20%, 100 mL) solution. The reaction mixture was extracted with ethyl acetate (200 mL×2). Organic layers were collected, washed with aq. sodium chloride (20%, 100 mL) solution and dried over sodium sulphate. Solvent was evaporated from resulting organic layer under reduced pressure and purified by column chromatography to give 2.05 g (76.13%) of 9-bromo-3-cyano-6,6-dimethyl-11-oxo-6,11-dihydro-5H-benzo[b]carbazole-8-yl-trifluoromethanesulfonate.

Step II: Preparation of 9-bromo-6,6-dimethyl-8-(4-morpholinopiperidin-1-yl)-11-oxo-6,11-dihydro-5H-benzo-[b]carbazole-3-carbonitrile To a solution of 9-bromo-3-cyano-6,6-dimethyl-11-oxo-6,11-dihydro -5H-benzo[b]carbazole-8-yl-trifluoro-methanesulfonate (1.8 g) in N-methyl-2-pyrrolidone (29.5 ml), 4-(piperdine-4-yl)morpholine (2.56 g) was added and reaction mixture was stirred at 118-120° C. for 3 hours. Thereafter, the reaction mixture was cooled and water (59 ml) was added. Resulting reaction mixture was filtered, washed with water and dried under reduced pressure to give 1.17 g (62.54%) of 9-bromo-6,6-dimethyl-8-(4-morpholinopiperidin-1-yl)-11-oxo-6, 11-dihydro-5H-benzo-[b]carbazole-3-carbonitrile.

Step III: Preparation of 9-ethynyl-6,6-dimethyl-8-(4-morpholinopiperdin-1-yl) -11-oxo-6,11-dihydro-5H-benzo[b]carbazole-3-carbonitrile A mixture of 9-bromo-6,6-dimethyl-8-(4-morpholinopiperidin-1-yl)-11-oxo -6,11-dihydro-5H-benzo-[b]carbazole-3-carbonitrile (1.0 g), triisopropylsilane acetylene (0.51 g), cesium carbonate (2.74 g), 2-dicyclohexylphosphino-2',4',6'-triisopropylbiphenyl (X-phos) (0.26 g) and bis(acetonitrile) dichloropalladium(II) (0.048 g) was stirred in acetonitrile (37.5 ml) at 80° C. for 15 hours. The reaction mixture was cooled and ethyl acetate (250 ml) was added. The resulting reaction mixture was washed with aq. sodium chloride (10%, 100 ml) solution. The organic layer was collected, dried over sodium sulphate, and concentrated under reduced pressure. The resulting residue was further dissolved in tetrahydrofuran (75 ml). Tetrabutylammonium fluoride (2.81 ml) was added to the reaction mass and stirred for 1 hour. Thereafter, ethyl acetate (250 ml) was added and organic layer was washed with water (50 ml×6) followed by aq. sodium chloride (10%, 50 ml) solution. Organic layer was dried over sodium sulphate and concentrated under reduced pressure. The residue was added to methanol (37.5 ml) and reaction mixture was filtered. The resulting product was washed with n-hexane (10 ml×2), dried under reduced pressure at 45-50° C. for 12-14 hours to give 0.625 g (69.66%) of 9-ethynyl-6,6-dimethyl-8-(4- morpholinopiperdin-1-yl)-11-oxo-6,11-dihydro-5H-benzo[b]carbazole-3-carbonitrile.

Step IV: Preparation of Alectinib

To a solution of 9-ethynyl-6,6-dimethyl-8-(4-morpholinopiperdin-1-yl)-11-oxo-6,11-dihydro-5H-benzo[b]carbazole-3-carbonitrile (0.6 g) in methanol (28 ml) : THF (42 ml), Pd-C(0.36 g) was added and stirred in a hydrogenator under hydrogen gas pressure for 3.5 hours. The reaction mixture was filtered through Celite bed and the filtrate was concentrated under reduced pressure at 40° C. The resulting material was purified by column chromatography (dichloromethane:methanol) to give 0.245 g (40.49%) of Alectinib.

XRPD pattern of Alectinib obtained after column chromatography is shown in FIG. 1 (Form A).

Overall yield of Alectinib obtained by above process is 13.43%.

Example-1: Preparation of Alectinib

Step I: Preparation of 9-bromo-3-cyano-6,6-dimethyl-11-oxo-6,11-dihydro -5H-benzo[b]carbazole-8-yl-trifluoromethanesulfonate A reaction mixture of 9-bromo-8-hydroxy-6,6-dimethyl-11-oxo-6,11-dihydro-5H -benzo[b]carbazole-3-carbonitrile (50.0 g) in dichloromethane (750 ml) and pyridine (62.2 g) was cooled to 0-5° C. and a solution of trifluoromethanesulfonic anhydride (111.0 g) in dichloromethane (250 ml) was added to the reaction mixture. Thereafter, reaction mixture was quenched with aq. 5% ammonium chloride solution, layers were separated and organic layer was dried over sodium sulphate followed by evaporation. The residue was taken in toluene (200 ml), stirred and filtered. The solid thus obtained was washed with toluene (2×50 ml), then with n-hexane (3×100 ml) and dried under vacuum to give 76.5 g (100%) of 9-bromo-3-cyano-6,6-dimethyl-11-oxo-6,11-dihydro-5H-benzo[b]carbazole-8-yl -trifluoromethanesulfonate.

Step II: Preparation of 9-bromo-6,6-dimethyl-8-(4-morpholinopiperidin-1-yl) -11-oxo-6,11-dihydro-5H-benzo[b] carbazole-3-carbonitrile A mixture of 4-(piperdine-4-yl) morpholine (89.5 g) and 9-bromo-3-cyano -6,6-dimethyl-11-oxo-6,11-dihydro-5H-benzo[b]carbazole-8-yl-trifluoro methanesulfonate (60.0 g) in dimethylacetamide (170 ml) was heated at 100-110° C. for 1.5 to 2 hours. Thereafter, reaction mixture was cooled to 60° C. and water (180 ml) was added. The solid was filtered, washed with water and dried under reduced vacuum at 40-45° C. for 10-12 hours to give 38.2 g (63.66%) of 9-bromo-6,6-dimethyl-8-(4-morpholinopiperidin-1-yl)-11-oxo-6,11-dihydro-5H-benzo-[b]carbazole-3-carbonitrile.

Step III: Preparation of Alectinib

To a solution of 9-bromo-6,6-dimethyl-8-(4-morpholinopiperidin-1-yl)-11-oxo-6,11-dihydro-5H-benzo-[b]carbazole-3-carbonitrile (2.0 g) in dimethylacetamide (20 ml), palladium acetate (0.08 g) and tricyclohexylphosphine (0.21 g) was added. The reaction mixture was stirred for 10-15 minutes at ambient temperature followed by addition of diethyl zinc (15% w/w solution in toluene, 6.8 ml). The reaction mixture was stirred for 2-3 hours at 40-45° C. and then cooled to room temperature followed by quenching with a mixture of hydrochloric acid (0.7 ml) and water (40 ml). The resulting product was filtered and dried at 50-55° C. for 10-12 hours. Solid thus obtained product was dissolved in methanol: dichloromethane (1:3, 40 ml), treated with activated carbon and filtered through Celite. The filtrate was distilled at atmospheric pressure and cooled to 0-5° C. The solid was filtered, washed with pre-cooled (0-5° C.) methanol (5.0 ml) and dried under vacuum at 50-55° C. for 10-12 hours to give 1.45 g (80.14%) of Alectinib.

Overall yield of Alectinib obtained by process of present invention is 51%.

Example 2: Preparation of 9-bromo-6,6-dimethyl-8-(4-morpholinopiperidin-1-yl)-11-oxo -6,11-dihydro-5H-benzo[b]carbazole-3-carbonitrile Step I: Preparation of 9-bromo-3-cyano-6,6-dimethyl-11-oxo-6,11-dihydro -5H-benzo[b]carbazole-8-yl-trifluoromethanesulfonate 9-bromo-8-hydroxy-6,6-dimethyl-11-oxo-6,11-dihydro-5H-benzo[b]carbazole-3-carbonitrile (1 kg) was added to a mixture of dichloromethane (14 L), pyridine (414.9 g) and trifluoromethanesulfonic anhydride (1480 g) at 0-10° C. The reaction mixture was stirred for 2-3 hours at 25-30° C. and evaporated till 5-7 volume. Hexane (30 L) was added to the resulting reaction mixture and stirred. The reaction mixture was filtered and washed with hexane (5 L) followed by water (20 L). The resulting product was dissolved in acetone (12 L) followed by addition of water (30 L) and stirred at 40-50° C. for 20-30 minutes. Thereafter, reaction mixture was cooled to ambient temperature, filtered, washed with water and dried under vacuum to give 9-bromo-3-cyano-6,6-dimethyl-11-oxo-6,11-dihydro -5H-benzo[1)]carbazole-8-yl-trifluoromethane-sulfonate.

Step II: Preparation of 9-bromo-6,6-dimethyl-8-(4-morpholinopiperidin-1-yl) -11-oxo-6,11-dihydro-5H-benzo[b] carbazole-3-carbonitrile 4-(Piperdine-4-yl) morpholine (3.57 kg) in N-methyl piperidine (3 L) was added to mixture of 9-bromo-3-cyano-6,6-dimethyl-11-oxo-6,11-dihydro -5H-benzo[b]carbazole-8-yl-trifluoro methanesulfonate in N-methyl piperidine (5 L) and stirred at 80-90° C. for 2 to 3 hours. Thereafter, reaction mixture was cooled to 50-60° C. and water (40 L) was added. The solid was filtered, washed with water and acetone. The resulting product was dried for 1-2 hours to give 1.1 kg (78.6%) of 9-bromo-6,6-dimethyl-8-(4-morpholinopiperidin-1-yl)-11-oxo-6,11-dihydro-5H-benzo-[b] carbazole -3-carbonitrile.

Example-3: Preparation of crystalline form B of Alectinib

Alectinib (1.7 g) was dissolved in methanol: dichloromethane (1:3, 40 ml), treated with activated carbon and filtered through Celite. The filtrate was distilled at atmospheric pressure and cooled to 0-5° C. The solid was filtered, washed with pre-cooled (0-5° C.) methanol (5.0 ml) and dried under vacuum at 50-55° C. for 10-12 hours to give 1.45 g of crystalline form B of Alectinib.

XRPD peaks: 8.565, 10.604, 12.616, 14.035, 21.659, 22.751 and 23.402±0.2° 2θ

Example-4: Preparation of Alectinib Hydrochloride (Type I)

Method A: To a mixture of Alectinib (700 mg) in methanol:dichloromethane (1:3) (28 ml) at 20-25° C., 2N hydrochloric acid (1.4 ml) was added and stirred for 20-30 minutes. Dichloromethane was evaporated under atmospheric pressure and methanol (0.7 ml) was added to the solid mass. The reaction mass was cooled to 0-5° C. and stirred for 30-40 minutes followed by filtration and washing with pre-cooled (0-5° C.) methanol (5 ml). The resulting product was dried under vacuum at 50-60° C. for 12-15 hours to give 590 mg of Alectinib hydrochloride having 99% purity by HPLC.

Method B: To a mixture of Alectinib (600 mg) in isopropanol (28 ml) at 60-70° C., 2N hydrochloric acid (1.2 ml) was added and stirred for 30-40 minutes. The reaction mass was cooled to 0-10° C. and further stirred for 30-40 minutes followed by filtration and washing with pre-cooled (0-5° C.) isopropanol (5 ml). The resulting product was dried under vacuum at 50-60° C. for 12-15 hours to give 510 mg of Alectinib hydrochloride having 99% purity by HPLC.

Method C: A mixture of Alectinib (700 mg), methyl ethyl ketone (7.0 ml), water (2.8 ml) and acetic acid (2.1 ml) was heated to 60° C. and 2N hydrochloric acid (0.7 ml) was added to the resulting mixture. The reaction was stirred for 30-35 minutes at 60° C. followed by addition of ethanol (17.5 ml). The resulting mixture was stirred for 30-40 minutes at 20-25° C. and further 30 minutes at 0-5° C. The solid was filtered, washed with pre-cooled (0-5° C.) ethanol (2.0 ml×2) and suck dried for 1-2 hours. The resulting product was dried under vacuum at 50-60° C. for 12-15 hours to give 590 mg of Alectinib hydrochloride having 99% purity by HPLC.

Method D: A mixture of Alectinib (1 kg), methyl ethyl ketone (10 L), water (4.8 L) and acetic acid (3.0 L) was heated to 60° C. and hydrochloric acid solution (181.81 ml in 818.19 ml water) was added to the resulting mixture. The reaction was stirred for 1 to 1.5 hours at 55-65° C. followed by addition of isopropanol (25 L). The resulting mixture was stirred for 2-3 hours at ambient temperature, filtered, washed with isopropanol and suck dried for 2-3 hours. The resulting product was dried under vacuum at 60-65° C. to give 850 g of Alectinib hydrochloride.

Example-5: Preparation of Alectinib hydrochloride (Form IV)

To a mixture of Alectinib (700 mg) in acetone (28 ml) at 50-55° C., 2N hydrochloric acid (1.4 ml) was added and stirred for 30-40 minutes. The reaction mass was cooled to 0-10° C. and further stirred for 30-40 minutes followed by filtration and washing with pre-cooled (0-5° C.) acetone (5 ml). The resulting product was dried under vacuum at 50-60° C. for 12-15 hours to give 620 mg of crystalline form IV of Alectinib hydrochloride having 99% purity by HPLC.

XRPD peaks: 5.538, 13.862, 15.088, 16.013, 19.958, 23.950 and 24.839±0.2° 2θ

Acetone content: 2.67%

Example-6: Preparation of Alectinib hydrochloride (Form V)

To a mixture of Alectinib (700 mg) in ethyl acetate (28 ml) at 70° C., 2N hydrochloric acid (2.1 ml) was added and stirred for 30-40 minutes. The reaction mass was cooled to ambient temperature and further stirred for 30-40 minutes followed by filtration and washing with ethyl acetate (10 ml). The resulting product was dried under vacuum at 50-60° C. for 12-15 hours to give 620 mg of crystalline form V of Alectinib hydrochloride having 99% purity by HPLC.

XRPD peaks: 11.455, 11.978, 14.298, 15.558, 20.051, 21.665, 23.331 and 25.017±0.2° 2θ

Example-7: Preparation of Alectinib hydrochloride (Form VI)

To a mixture of Alectinib (700 mg) in acetonitrile (28 ml) at 60-65° C., 2N hydrochloric acid (1.4 ml) was added and stirred for 30-40 minutes. The reaction mass was cooled to 0-10° C. and further stirred for 30-40 minutes followed by filtration and washing with pre cooled (0-5° C.) acetonitrile (5 ml). The resulting product was dried under vacuum at 50-60° C. for 12-15 hours to give 590 mg of crystalline form VI of Alectinib hydrochloride having 99% purity by HPLC.

XRPD peaks: 5.697, 14.764, 18.664, 20.151, 22.320 and 23.334±0.2° 2θ

We claim:
1. A process for preparing Alectinib of formula I,

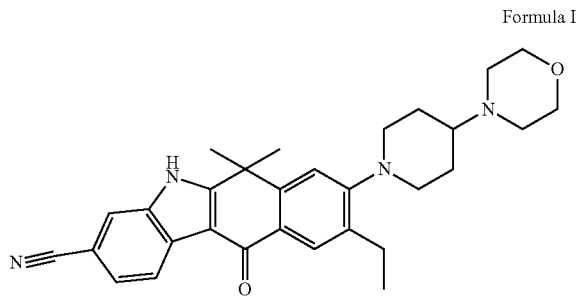 [SMILES: CCc1cc2c(cc1N1CCC(N3CCOCC3)CC1)C(C)(C)c1[nH]c3cc(C#N)ccc3c1C2=O]

Formula I or a pharmaceutically acceptable salt thereof, the process comprising reacting a compound of formula II, Formula II wherein X is halo, with diethylzinc.

2. The process according to claim 1, wherein the reaction is performed in the presence of a catalyst.

3. The process according to claim 2, wherein the catalyst comprises a palladium (II) catalyst.

4. The process according to claim 3, wherein the palladium (II) catalyst comprises palladium(II) acetate, [1,2-bis (diphenylphosphino)ethane]dichloropalladium(II), or [1,1'-bis(diphenylphosphino)ferrocene]palladium(II) dichloride.

5. The process according to claim 4, wherein the palladium (II) catalyst comprises palladium (II) acetate.

6. The process according to claim 1, wherein the reaction is performed in the presence of a catalyst and a ligand.

7. The process according to claim 6, wherein the ligand comprises a phosphine ligand.

8. The process according to claim 7, wherein the phosphine ligand comprises tricyclohexylphosphine, tri-tert-butylphosphine, triphenylphosphine, or 2-dicyclohexylphosphino-2',4',6'-triisopropylbiphenyl.

9. The process according to claim 8, wherein the phosphine ligand comprises tricyclohexylphosphine.

10. The process according to claim 6, wherein the catalyst comprises palladium(II) acetate, [1,2-bis(diphenylphosphino)ethane]-dichloropalladium(II), or [1,1'-bis(diphenylphosphino) ferrocene]palladium(II) dichloride.

11. The process according to claim 1, wherein the reaction is performed in the presence of a solvent comprising one or more amide solvents, sulfoxide solvents, ethers, or a mixture thereof.

12. The process according to claim 11, wherein the solvent comprises N-methylpyrrolidone, dimethyl sulfoxide, dimethylacetamide, diethylacetamide, dimethylformamide, dioxane, tetrahydrofuran, or a mixture thereof.

13. The process according to claim 1, wherein the reaction is performed in the presence of a catalyst, a ligand, and a solvent.

14. The process according to claim 13, wherein the catalyst comprises a palladium (II) catalyst, the ligand comprises a phosphine ligand, and the solvent comprises one or more amide solvents, sulfoxide solvents, ethers, or a mixture thereof.

15. The process according to claim 14, wherein the palladium (II) catalyst comprises palladium (II) acetate, the phosphine ligand comprises tricyclohexylphosphine, and the solvent comprises dimethylacetamide.

16. The process according to claim 1, further comprising converting Alectinib to Alectinib hydrochloride.

17. The process according to claim 16, further comprising combining the Alectinib hydrochloride with one or more pharmaceutically acceptable excipients to provide a pharmaceutical composition.

18. The process according to claim 13, further comprising converting Alectinib to Alectinib hydrochloride.

19. The process according to claim 18, further comprising combining the Alectinib hydrochloride with one or more pharmaceutically acceptable excipients to provide a pharmaceutical composition.

20. The process according to claim 14, further comprising converting Alectinib to Alectinib hydrochloride.

21. The process according to claim 20, further comprising combining the Alectinib hydrochloride with one or more pharmaceutically acceptable excipients to provide a pharmaceutical composition.

22. The process according to claim 15, further comprising converting Alectinib to Alectinib hydrochloride.

23. The process according to claim 20, further comprising combining the Alectinib hydrochloride with one or more pharmaceutically acceptable excipients to provide a pharmaceutical composition.

* * * * *